US012380973B1

(12) United States Patent
Venkatraman et al.

(10) Patent No.: US 12,380,973 B1
(45) Date of Patent: Aug. 5, 2025

(54) SYSTEMS AND METHODS FOR DICTATION WITH A DIGITAL STETHOSCOPE

(71) Applicant: Eko Health, Inc., Emeryville, CA (US)

(72) Inventors: Subramaniam Venkatraman, Emeryville, CA (US); Michael Childs, Palm Springs, CA (US); Dan Freschl, Albany, CA (US); Theo Brower, Berkeley, CA (US); Shanmugam Muruga Palaniappan, Berkeley, CA (US); Connor Landgraf, Martinez, CA (US)

(73) Assignee: EKO HEALTH, INC., Emeryville, CA (US)

( * ) Notice: Subject to any disclaimer, the term of this patent is extended or adjusted under 35 U.S.C. 154(b) by 0 days.

(21) Appl. No.: 18/908,579

(22) Filed: Oct. 7, 2024

(51) Int. Cl.
| A61B 7/04 | (2006.01) |
| A61B 5/00 | (2006.01) |
| A61B 5/318 | (2021.01) |
| A61B 5/332 | (2021.01) |
| A61B 5/335 | (2021.01) |
| G16H 10/60 | (2018.01) |

(52) U.S. Cl.
CPC .......... G16H 10/60 (2018.01); A61B 5/0006 (2013.01); A61B 5/332 (2021.01); A61B 7/04 (2013.01); A61B 2562/06 (2013.01)

(58) Field of Classification Search
CPC ........ G16H 10/60; G16H 10/65; G16H 10/00; A61B 5/332; A61B 5/333; A61B 5/335; A61B 5/318; A61B 5/316; A61B 5/24; A61B 5/0006; A61B 7/04; A61B 7/026; A61B 7/02; A61B 7/00; A61B 2562/00; A61B 2562/0204; A61B 2562/02; A61B 2562/04; A61B 2562/06

See application file for complete search history.

(56) References Cited

U.S. PATENT DOCUMENTS

| 5,025,809 A * | 6/1991 | Johnson ................... A61B 7/04 600/528 |
| 5,492,129 A * | 2/1996 | Greenberger ............ A61B 7/04 600/528 |
| 7,346,174 B1 * | 3/2008 | Smith ..................... G16H 40/63 600/528 |
| 9,265,478 B2 * | 2/2016 | Wang ........................ A61B 7/04 |
| 10,052,081 B2 * | 8/2018 | Rajagopal .......... A61B 5/02055 |
| 10,342,444 B2 * | 7/2019 | Albert .................... A61B 5/316 |

(Continued)

*Primary Examiner* — Edgardo San Martin
(74) *Attorney, Agent, or Firm* — McCoy Russell LLP

(57) ABSTRACT

The present description relates to methods and systems for a medical dictation. In one example, a stethoscope includes a first microphone positioned to capture physiological sounds of a patient, a second microphone positioned to capture ambient sounds, one or more processors, and memory storing instructions executable by the one or more processors to: during a stethoscope mode, obtain a first signal from the first microphone and a second signal from the second microphone, process the first signal to capture a physiological sound signal, including performing noise cancellation on the first signal based on the second signal, and transmit the physiological sound signal to an external computing device and/or a speaker of the stethoscope; and during a dictation mode, obtain the second signal from the second microphone, process the second signal to capture a voice signal, and transmit the voice signal to the external computing device.

20 Claims, 10 Drawing Sheets

(56) References Cited

U.S. PATENT DOCUMENTS

| | | | |
|---|---|---|---|
| 11,741,931 B2* | 8/2023 | Donovan | G10K 11/17823 |
| | | | 381/67 |
| 12,029,606 B2* | 7/2024 | Adler | A61B 5/742 |
| 2008/0013747 A1* | 1/2008 | Tran | A61B 7/04 |
| | | | 381/67 |
| 2009/0312638 A1* | 12/2009 | Bartlett | A61B 8/4427 |
| | | | 600/443 |
| 2017/0296053 A1* | 10/2017 | Thiagarajan | A61B 5/282 |
| 2018/0315428 A1* | 11/2018 | Johnson | G10L 15/26 |
| 2020/0121277 A1* | 4/2020 | Hyde | A61B 7/00 |
| 2021/0259560 A1* | 8/2021 | Venkatraman | A61B 5/024 |
| 2021/0275037 A1* | 9/2021 | Shallom | A61B 7/026 |
| 2021/0345934 A1* | 11/2021 | Landgraf | A61B 5/6898 |
| 2022/0354451 A1* | 11/2022 | Venkatraman | A61B 5/7264 |
| 2024/0188836 A1* | 6/2024 | Chou | A61B 5/282 |

\* cited by examiner

SYSTEMS AND METHODS FOR DICTATION WITH A DIGITAL STETHOSCOPE

FIELD

The present description relates generally to methods and systems for using a digital stethoscope for dictation and scribing.

BACKGROUND/SUMMARY

Medical practitioners take notes for several reasons, including documenting patient care, providing legal protection, communicating with other healthcare providers, tracking patient progress, and facilitating billing and insurance processes. However, the task of note-taking presents numerous challenges for practitioners. Time constraints during patient visits, the need for accuracy and detail, balancing patient interaction with documentation, the complexity of medical information, and potential distractions in a clinical setting all contribute to making accurate note-taking difficult.

To address these challenges, practitioners have adopted various dictation methods to streamline the note-taking process. These methods include traditional dictation using recording devices for later transcription, real-time transcription services with human transcriptionists, speech recognition software that converts speech to text, mobile apps designed for medical dictation, and the use of scribes who take notes during patient encounters.

However, the inventors herein have recognized potential issues with existing dictation methods. As one example, current dictation methods necessitate additional personnel, hardware, or software tools, each of which may add expense to a patient visit. Further, some dictation methods demand extra clinician time. Additionally, some dictation methods may demand a clinician use their personal mobile device, which may pose security and privacy issues.

In one example, the issues described above may be addressed by a dictation stethoscope that includes a first microphone positioned to capture physiological sounds of a patient, a second microphone positioned to capture ambient sounds in an environment surrounding the dictation stethoscope, one or more processors, and memory storing instructions executable by the one or more processors to: during a stethoscope mode, obtain a first signal from the first microphone and a second signal from the second microphone, process the first signal to capture a physiological sound signal, the processing including performing noise cancellation on the first signal based on the second signal, and transmit the physiological sound signal to an external computing device and/or a speaker of the dictation stethoscope; and during a dictation mode, obtain the second signal from the second microphone, process the second signal to capture a voice signal, and transmit the voice signal to the external computing device.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1A:
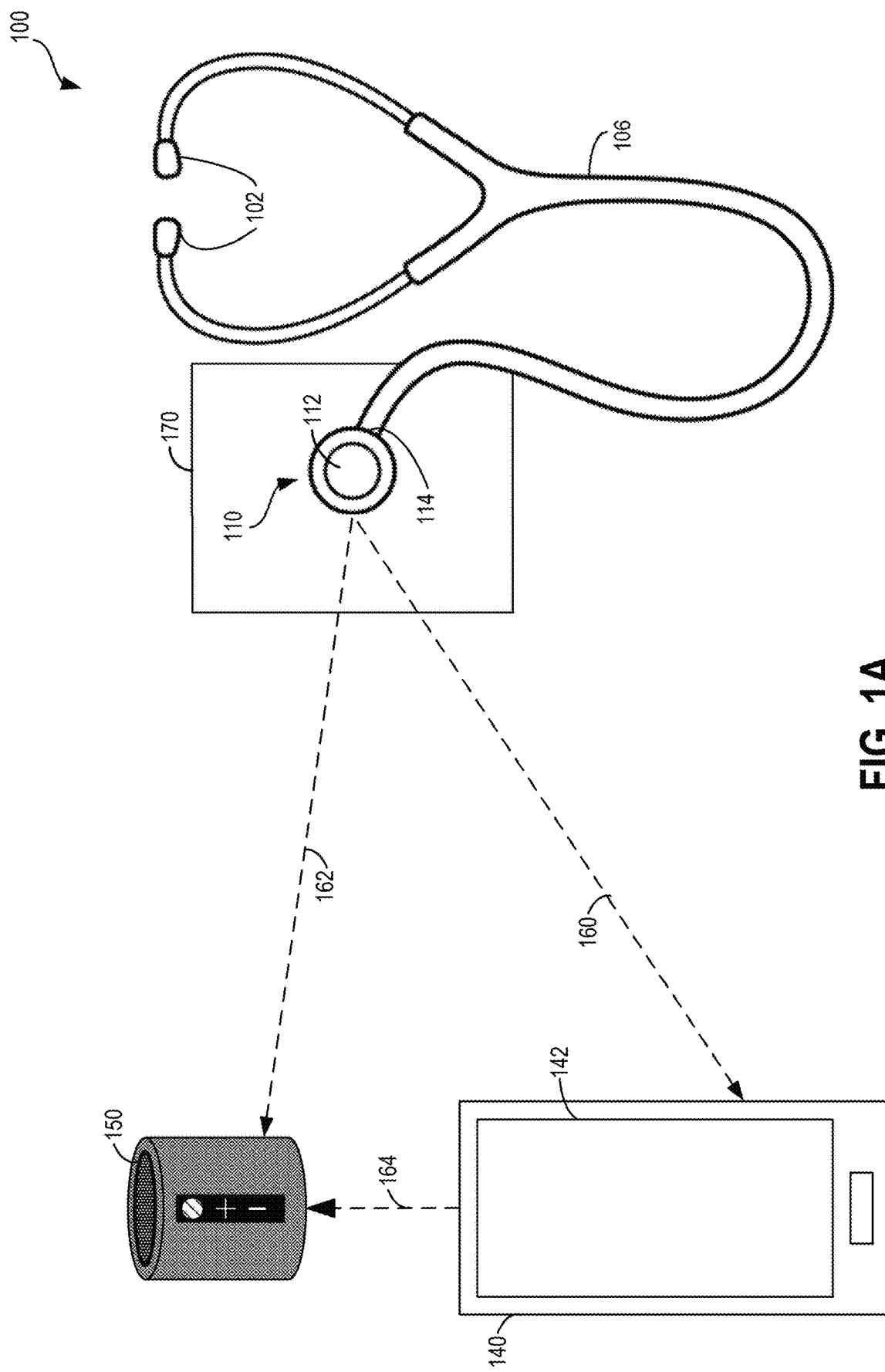
FIG. 1A is a schematic drawing showing an example stethoscope including earpieces connected to a chestpiece.

The present description relates generally to methods and systems for a digital stethoscope configured to be used as a dictation device with automated voice-to-text capabilities. A digital stethoscope configured to be used as a dictation device (which may be referred to herein as a dictation stethoscope) may remove the need for a practitioner (such as a doctor, nurse, physician assistant, etc.) to carry extra hardware such as a recording device and also negates the need for the practitioner to user their personal mobile device for the purposes of dictation during a patient encounter.

As explained previously, practitioners may utilize various mechanisms to take notes during patient encounters, such as manually taking notes on paper or a computer, utilizing a recording device, and the like. However, each method presents its own challenges and drawbacks, such as demanding the practitioner carry extra hardware or posing security or patient privacy risks. Thus, a dictation stethoscope as disclosed herein may be used to obtain voice recordings during a patient encounter, when the stethoscope is not being used to record physiological sounds (e.g., heart or lung sounds). Digital stethoscopes may offer several advantages over prior methods of dictation. Digital stethoscopes may travel with practitioners throughout their working day and thus may be easily accessible during most patient encounters, thereby avoiding the need for practitioners to carry a separate, dedicated dictation device or use a personal device. Further, digital stethoscopes may include an external-facing microphone for the purposes of noise cancellation, which is positioned in a suitable location for recording voice information. Further, digital stethoscopes may be integrated in an ecosystem that may facilitate secure storage and distribution of voice recordings obtained during patient encounters. For example, digital stethoscopes may already be configured to transmit audio data to an external computing device, which may then store and/or process the audio data and send the audio data to a remote analysis system for further processing (such as to identify clinical findings) and/or to a database for long-term storage, accessible to practitioners to enable annotation and playback of the audio data.

However, standard digital stethoscopes are not fully equipped to record and transmit voice recordings at sufficient quality to facilitate accurate transcriptions of the voice recordings. Thus, according to embodiments disclosed herein, a dictation stethoscope may be specifically configured to obtain both high-quality heart and/or lung sound recordings and high-quality voice recordings, and transmit both to an external computing device for additional processing and/or storage. For example, the dictation stethoscope disclosed herein may be configured to operate in multiple operating modes. During a stethoscope mode where the dictation stethoscope is positioned to capture heart sounds (e.g., a chestpiece of the stethoscope is positioned on a chest of a patient), the dictation stethoscope may obtain output from a first microphone positioned to capture the heart sounds and obtain output from a second microphone positioned to capture ambient sounds, and use the signal from the second microphone to perform noise cancellation on the signal from the first microphone. During a dictation mode where the dictation stethoscope is not being used to capture heart sounds and a user of the dictation stethoscope desired to record voice sounds, the dictation stethoscope may deactivate the first microphone and obtain output from the second microphone (e.g., at a second rate). In both modes, the obtained audio (e.g., heart sound recordings in the stethoscope mode and voice recordings in the dictation mode) may be transmitted to an external computing device for further processing and/or storage.

The audio obtained during the stethoscope mode (e.g., heart sound recordings, after noise cancellation) may be compressed according to a first compression process (e.g., lossless) while the audio obtained during the dictation mode (e.g., the voice recordings) may be compressed according to a second compression process (e.g., lossy). Additionally, the audio obtained during the stethoscope mode may be downsampled relative to the audio obtained during the dictation mode, such that the audio obtained during the stethoscope mode is transmitted to the external computing device at a lower sampling rate than the audio obtained during the dictation mode. The different sampling/transmission rates and compression processes in the two modes of operation may ensure high quality voice recordings are captured and transmitted during the dictation mode while still preserving battery life during the stethoscope mode and capturing heart sound recordings that can be analyzed and processed with existing analysis models.

Figure 1B:
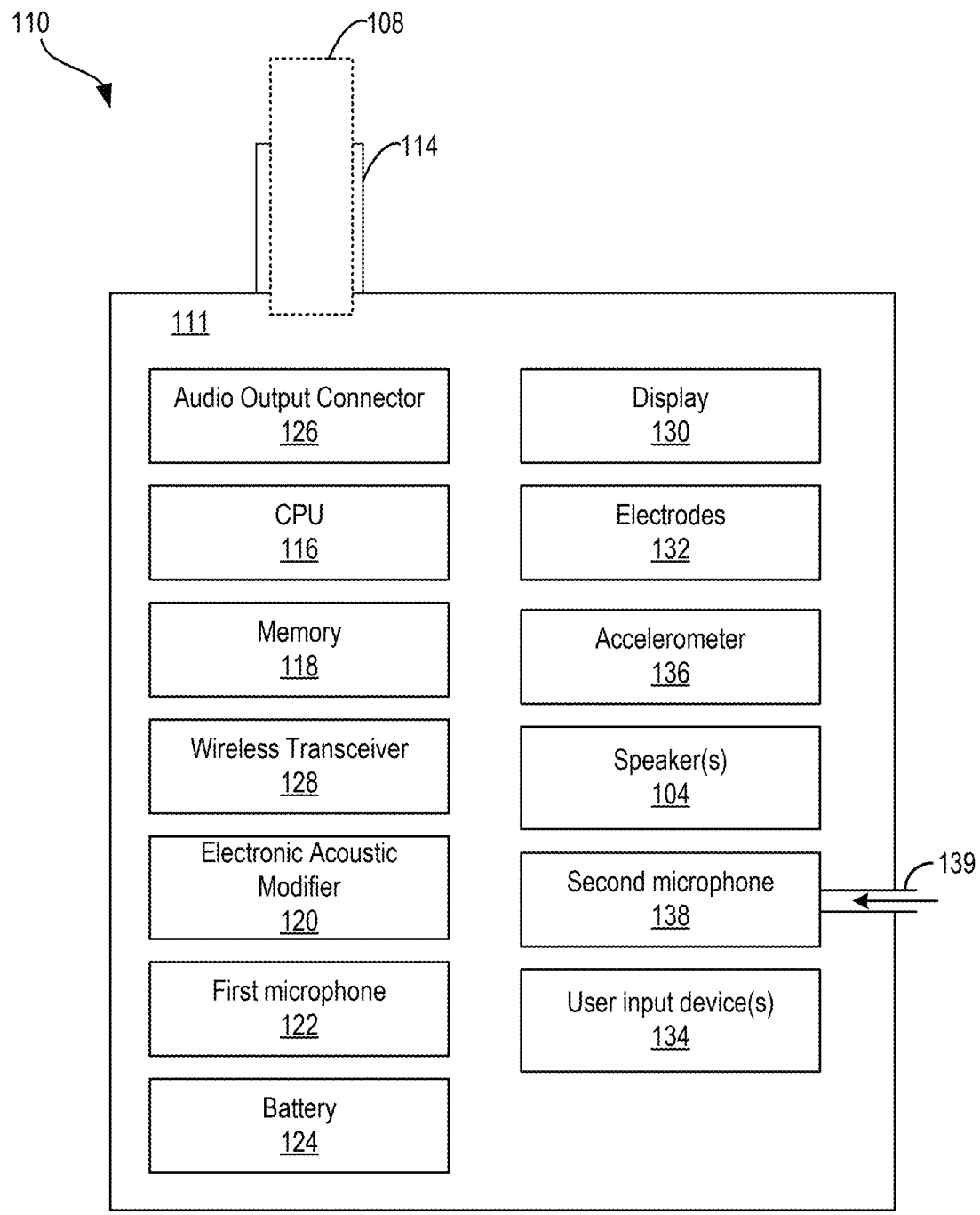
FIG. 1B is a block diagram showing the components of the chestpiece shown in FIG. 1A.

Turning now to the figures, FIGS. 1A and 1B show a dictation stethoscope 100 that may be used to collect heart sound recordings of a patient in a stethoscope mode and used to collect voice recordings when in a dictation mode. The dictation stethoscope 100 shown in FIGS. 1A and 1B is one example of an electronic stethoscope that may be used to collect physiological sound recordings such as heart sound recordings, collect voice recordings, and transmit the physiological sound and voice recordings to an external computing device for further processing as disclosed herein. It is to be appreciated that other electronic stethoscopes that are configured to collect physiological sound recordings may be used without departing from the scope of this disclosure.

Referring first to FIG. 1A, the dictation stethoscope 100 includes a chestpiece 110 and an output tube 106. The chestpiece 110 is in electronic communication with the output tube 106 through a connector 114 of the chestpiece. The output tube 106 includes earpieces 102 configured to be positioned in ears of a wearer to project recorded physiological sounds to the wearer. The output tube 106 and earpieces 102 may form a headset.

The chestpiece 110 may include a diaphragm 112, which is a sealed membrane with air inside that vibrates from external noises. The diaphragm 112 moves a volume of air inside the chestpiece 110 according to the vibrations caused by the external noises, which in turn creates sounds that may be recorded and transmitted through the connector 114 to the output tube 106. In some examples, the chestpiece 110 may include a bell in addition to the diaphragm 112. When included, the bell may be an open hollow cup or may include a smaller sealed membrane than the diaphragm 112, and air inside the bell may vibrate from external noises to produce acoustic pressure waves. The diaphragm 112 may be used for higher frequency auscultation, such as heart beats and breath sounds, while the bell may be used for lower frequency auscultation, such as heart murmurs and bowel sounds. The chestpiece 110 may be placed on a patient (e.g., subject) 170 by the patient 170 or by a clinician (not shown) for auscultation. The clinician or the patient 170 may listen to bodily sounds produced by the patient through the earpieces 102.

In some examples, the dictation stethoscope includes one or more speakers to transmit amplified audio to a user's ears. The one or more speakers may be positioned in the chestpiece 110, in the output tube 106, or at the earpieces 102. Additional detail about the one or more speakers is provided below with respect to FIG. 1B.

The chestpiece 110 may connect to other electronic devices through wireless connections. For example, the chestpiece 110 may connect to an external computing device 140 through a first wireless connection 160. The external computing device 140 may be a mobile device, such as a smartphone, a tablet, a smartwatch, a laptop computer, or a personal digital assistant (PDA), for example. Alternatively, the external computing device 140 may be a stationary device, such as a desktop computer or server. In still other examples, the external computing device 140 may be included in a computing network, such as a cloud computing network. The external computing device 140 may include a processor operatively connected to memory (such as random-access memory, read-only memory, flash memory, a hard disk, etc.) as well as a communications interface for sending/receiving wired or wireless signals from a network and/or other computing devices, including the chestpiece 110. Further, the external computing device 140 includes a user interface 142, such as a display for outputting information to a user and one or more of a touchscreen, a trackball, hard keys/buttons, a keyboard, a mouse, and a trackpad for receiving user inputs. The external computing device 140 may operate a software application that receives the user inputs via the user interface 142 to adjust operation of the chestpiece 110. By connecting wirelessly to the external computing device 140, the chestpiece 110 may send audio data, and optionally other physiological data (e.g., accelerometer data, electrocardiogram data) to the external computing device 140. The audio data collected by the chestpiece 110 and sent to the external computing device 140 may include heart sound recordings and voice recordings, depending on the mode of operation, as described in more detail below.

As another example, the chestpiece 110 may connect to an external listening device 150 through a second wireless connection 162, and sounds recorded by the chestpiece 110 may be projected by the external listening device 150 for the patient 170 or the clinician to hear. The external listening device 150 may be a speaker, headphones, earbuds, hearing aids, or another device capable of projecting sound and forming wireless connections to other devices. In some examples, the external computing device 140 may connect to the external listening device 150 through a third wireless connection 164 instead of the chestpiece 110 connecting directly to the external listening device 150. In such examples, recorded sounds may be sent from the chestpiece 110 to the external computing device 140 and from the external computing device 140 to the external listening device 150.

As will be elaborated below with respect to FIG. 1B, the chestpiece 110 includes components for recording and sharing auscultations (e.g., heart sound recordings) and for recording and sharing voice recordings (e.g., dictation recordings). Additionally, in some examples, the chestpiece 110 may include components for recording and sharing electronic signals of a heart (e.g., electrocardiogram signals). Further, in some examples, the chestpiece 110 may be disconnected from the output tube 106 and the earpieces 102.

Continuing to FIG. 1B, in some examples, the chestpiece 110 includes a body 111 that houses internal components, examples of which are elaborated below. The chestpiece 110 includes a computer processing unit (CPU) 116, such as a microcontroller unit (MCU), positioned within the body 111. The CPU 116 receives inputs and/or sends outputs to various electronic components that will be described further herein. In some examples, the body 111 includes one microdevice that contains the CPU 116 and some or all of the electronic and electrical components. In some arrangements, the CPU 116 and the electronic and electrical components are positioned on two or more microdevices. The CPU 116 is operatively coupled to a memory 118, which includes one or more of a non-transitory (e.g., read-only) memory, a keep alive memory, and a random-access memory.

The chestpiece 110 may include an electronic acoustic modifier 120 in electrical communication with the CPU 116. In some examples, the electronic acoustic modifier 120 is a stand-alone device. In other examples, the electronic acoustic modifier 120 is firmware within the CPU 116. The electronic acoustic modifier 120 is configured to receive an electronic signal from a first microphone 122 (e.g., the signal output by the first microphone 122, which includes a digitized signal of vibrations of the volume of air generated by the diaphragm during auscultation), modify the electronic signal to form a modified electronic signal (e.g., amplify the electronic signal), and transmit the modified electronic signal to one or more speakers 104 configured to convert the modified electronic signal to sound output. The electronic signal captured by the first microphone 122 may be visually represented as a phonocardiogram (PCG) signal that can be transmitted to one or more external devices, as explained below. Further, the first microphone 122 may include an analog-to-digital converter (ADC) that digitizes the analog signal generated by the first microphone into the electronic signal.

The one or more speakers 104 may be positioned in the chestpiece 110, as shown. In such examples, the one or more speakers 104 may convert the electronic signal (e.g., received from the electronic acoustic modifier 120) to a sound output that is transmitted to a user's ears via the output tube 106 and earpieces 102. In other examples, the one or more speakers may be positioned elsewhere, such as within the output tube 106 or within the earpieces 102.

The chestpiece 110 includes an optional audio output connector 126, such as a headphone jack or USB-type port, which can receive the modified electronic signal from the electronic acoustic modifier 120. A user may physically connect a peripheral device to the audio output connector 126. Examples of such peripheral devices include but are not limited to a computer, a cell phone, and a listening device configured to convert the modified electronic signal to sound. The audio output connector 126 may also act as a charging port in order to charge battery 124 of chestpiece 110.

In some examples, a wireless transceiver 128 is positioned in the chestpiece 110, such as within the body 111, as shown. In some examples, the wireless transceiver 128 may be included in a circuit board, such as a printed circuit board (PCB), that may also include one or more electronic components, such as the first microphone 122 and the CPU 116. The wireless transceiver 128 is in electrical communication with the electronic acoustic modifier 120. The wireless transceiver 128 is configured to receive the modified electronic signal from the electronic acoustic modifier 120, convert the modified electronic signal to a modified wireless signal, and wirelessly transmit the modified wireless signal from the chestpiece to an external listening device, such as the external listening device 150 shown in FIG. 1A, and/or a peripheral device, such as external computing device 140 shown in FIG. 1A. The wireless transceiver 128 may use any appropriate communication types and protocol, such as television, cellular phone, Wi-Fi, satellite, two-way radio, infrared, short-range microwave signals, IEEE 802.11 compliant radio signals, Bluetooth®, Low Energy Bluetooth (BLE), and/or BLE audio. In some examples, the wireless transceiver 128 may be configured to pair directly to the external listening device 150 and/or the external computing device 140. Alternatively, the wireless transceiver 128 may communicate data to the external listening device 150 and/or the external computing device 140 through an intermediary device, such as a wireless router maintaining a local area network (WLAN) or through a connection to the internet. The wireless transceiver 128 may also be configured to receive signals from one or more peripheral devices, including the external computing device 140 shown in FIG. 1A. In some examples, the wireless transceiver 128 is in electrical communication with the first microphone 122, and can wirelessly transmit the electronic signal from the first microphone 122 to the external listening device 150 and/or the external computing device 140 without modification of the electronic signal via the electronic acoustic modifier 120. In some examples, the chestpiece 110 may include a second wireless transceiver that may thereby allow the chestpiece to establish two separate wireless connections with external devices. For example, the wireless transceiver 128 may connect to the external computing device 140 while the second wireless transceiver connects to the external listening device 150.

It may be understood that sound may be projected via the speaker(s) 104 and also transmitted via the wireless transceiver 128 at the same time. For example, a user (e.g., a clinician or the patient 170) may listen to physiological sounds while placing the electronic stethoscope on the patient 170 via the earpieces 102 while one or more remote clinicians listen simultaneously via the external listening device 150.

In some examples, the electronic signal from the first microphone 122 or the modified electronic signal may be analyzed on the chestpiece 110 by the CPU 116. In some examples, the electronic signal or the modified electronic signal may be transmitted by the wireless transceiver 128 or through the audio output connector 126 to the external listening device 150 and/or the external computing device 140. Such signals can then be analyzed on the external computing device 140 to extract information about the condition of the patient or to suggest the preliminary diagnosis. The results of such an analysis can be transmitted back to the wireless transceiver 128 and can be communicated to a user of the dictation stethoscope 100 visually or with sound. Visual information can be provided using via a display screen 130 of the chestpiece 110. Sound may be in the form of beeps, tones, or voice transmitted through the speakers 104 or the external listening device 150. The external listening device 150 may be wireless headphones, a hearing aid, or a wireless speaker, for example, which is not included within the dictation stethoscope 100.

In some examples, the chestpiece 110 includes a second microphone 138 facing the external environment. The second microphone 138 is configured to detect audio from the external environment (e.g., via a port 139) and to convert the audio into an electronic signal. In some examples, one or both of the first microphone 122 and the second microphone 138 is a micro-electrical-mechanical system (MEMS) microphone, an electret microphone, or a piezoelectric microphone. When such a second microphone 138 is included in the chestpiece, the electronic acoustic modifier 120 is configured to receive the electronic signal from the second microphone 138 and to use the electronic signal, for example, as part of active noise cancellation, in modifying the electronic signal from the first microphone 122 to form the modified electronic signal. The second microphone 138 may also include an ADC to covert the analog signal generated by the microphone to an electronic signal (e.g., to digitize the signal).

Examples of the kinds of electronic signal modifications that may be performed using the electronic acoustic modifier 120 include, but are not limited to, active noise cancellation, single channel noise reduction (SCNR), and upward or downward expansion. In an exemplary embodiment of the active noise cancellation, the electronic acoustic modifier 120 receives the electronic signal from the second microphone 138 and reduces the amplitude of or removes the noise component from the electronic signal received from the first microphone 122, thus increasing a quality of the modified electronic signal. SCNR refers to techniques which may reduce the noise portion of the modified electronic signal through the use of temporal, spectral, or statistical differences between the electronic signal from the first microphone 122 and the electronic signal from the second microphone 138. A downward expander can reduce the gain on a signal when the amplitude of a signal is below a pre-set threshold. In some examples, the gain is reduced to zero. Any gain reduction may minimize noise detection when the chestpiece 110 is held against the air.

In some examples, the second microphone 138 may be used when the digital stethoscope is operating in a dictation mode where sounds received by the second microphone 138 are transmitted to the external computing device 140. For example, during a stethoscope mode, the first microphone 122 and the second microphone 138 may both be active and the electronic signal collected with the second microphone 138 may be used to perform active noise cancellation on the electronic signal collected by the first microphone 122 to form the modified electronic signal, as explained above. The modified electronic signal may be sent to the external computing device 140 as a heart sound recording, for example. However, during the dictation mode, the first microphone 122 may be deactivated and the second microphone 138 may be activated. The electronic signal collected with the second microphone 138 during the dictation mode may be transmitted to the external computing device 140 and saved as a voice recording. The voice recording may be transcribed to text and eventually be saved in long-term storage and/or sent to a remote analysis system, as explained in more detail below.

Figure 9:
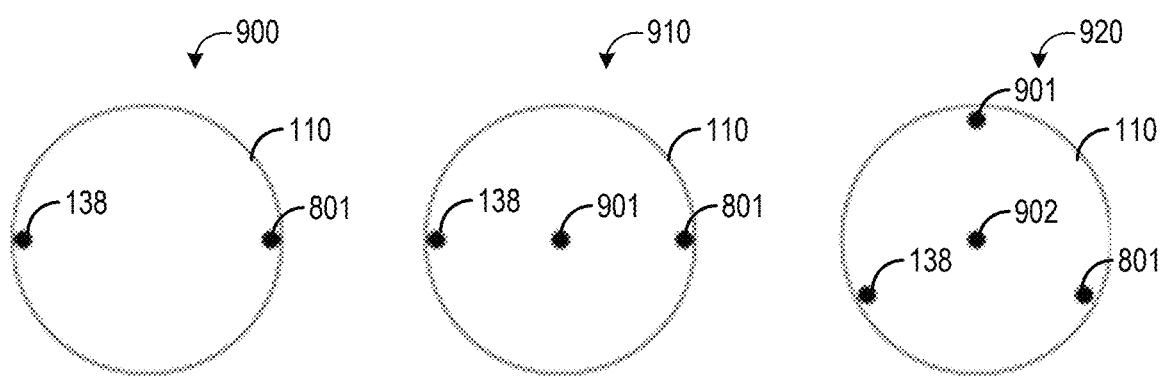
FIGS. 9-10B show example chestpiece configurations for the dictation stethoscope.

In still further examples, the second microphone 138 may comprise a microphone array including two or more second microphones. The microphone array may allow for beamforming to be performed, wherein the angle of incidence of sound can be calculated from the output of the microphone array and used to identify a primary speaker (e.g., a clinician operating the digital stethoscope) and ambient sounds. When in dictation mode, the audio from the primary speaker can be isolated and sent to the external computing device 140 and saved as a voice recording. When in ambient listening mode, the electronic signals corresponding to the ambient sounds may be sent to the external computing device 140 and saved as an ambient recording. The ambient recording may capture other voice(s) in the environment (beyond the primary speaker), such as a patient, another clinician, etc. In this way, the signals captured by the microphones of the microphone array may be post-processed to form directional patterns with peaks and nulls in sensitivity to improve signal to noise ratio (SNR) in desired directions. The post-processing may be carried out on the dictation stethoscope (e.g., on a microprocessor) as part of the audio digital signal processing. The microphones of the microphone array may be positioned around the outer edges of the dictation stethoscope (e.g., around the outer edges of the chestpiece) to provide physical separation between the microphones in either a linear or circular array with a minimum of two microphones in an array. Example arrangements for the microphones of the microphone array are shown in FIGS. 9 and 10.

It should be understood that, in describing electrical communication, the phrase, "A is in electrical communication with B," describes both direct electrical communication from A and B or from B and A and also electrical communication that goes between A to B through the CPU 116, (e.g., from A to the CPU 116 to B and from B to the CPU 116 to A).

Chestpiece 110 further includes a battery 124. The battery 124 may be a disposable battery or a rechargeable battery. If the battery 124 is a disposable battery, the outside of the chestpiece may include a door (not shown) through which the battery 124 can be changed. If the battery 124 is a rechargeable battery, the outside of the chestpiece may include a charging port (as explained above) through which the battery 124 can be charged. Alternatively, the battery 124 may be charged wirelessly. The battery 124 is configured to supply power to the electronic components of the chestpiece, including, but not limited to, the microphone first 122, the electronic acoustic modifier 120, the second microphone (when included), the speaker(s) 104, the CPU 116, the wireless transceiver 128, and the display screen 130.

Chestpiece 110 may also include one or more display outputs (not shown) positioned on an exterior of the chestpiece 110, such as indicator lights. In some examples, the display screen 130 configured to display text and/or images may also be included as a display output. The indicator lights and/or the display screen may provide information about the state of the dictation stethoscope 100 and/or provide information about the condition of the patient. For example, when the dictation stethoscope is operating in the dictation mode, an indicator light may be activated to indicate that a voice recording is in process.

In some examples, the chestpiece 110 includes one or more devices to provide audio indicator signals (not shown) to provide sounds, such as beeps or verbal language, to indicate device operation status and/or information about the condition of the patient. In some examples, the volume of the audio indicator can be adjusted or turned off through user inputs.

In some examples, the chestpiece 110 includes one or more user input devices 134. The one or more user input devices 134 may include one or more touch sensors positioned inside the body 111 of the chestpiece 110 (e.g., proximate to an exterior of the chestpiece) or on an outer surface of the body 111 of the chestpiece 110. The touch sensor(s) may be capacitive touch sensor(s) comprised of one or more capacitive touch-sensing elements (e.g., one or more electrodes coupled to an insulating material) coupled to a measurement circuit configured to detect a touch input based on detecting capacitance generated by a human finger, for example, touching the capacitive touch-sensing element. Additionally or alternatively, the touch sensor(s) may be resistive, impedance, or inductive touch sensor(s) coupled to a measurement circuit configured to detect a touch input (e.g., contact or proximity). The one or more user input devices 134 may additionally or alternatively include a button or switch. The output from the one or more user input devices 134 may be used to activate/power on the dictation stethoscope 100 and/or determine a mode of operation of the dictation stethoscope.

In some examples, the body 111 of the chestpiece 110 may be connected to the output tube 106 shown in FIG. 1A via a connector 108 of the output tube 106 that is configured to be positioned within connector 114 of the chestpiece 110. In some examples, connector 108 and connector 114 may enable electrical connection between signal wires in the output tube 106 and the electrical components of the chestpiece 110 (e.g., the electronic acoustic modifier 120). In other examples, the connector 108 may facilitate an acoustic connection between speaker(s) 104 in the chestpiece 110 and the output tube 106 and earpieces 102. Thus, the connector 114 may house connector 108 in order to mechanically and acoustically couple the earpieces 102 to the chestpiece 110. The connector 108 may be integrated with (e.g., part of) the output tube 106 or may be a separate fitting.

In some examples, one or more feedback signals may be used to determine whether or not the output tube 106/earpieces 102 are physically connected to the chestpiece 110. For example, the CPU 116 may receive feedback from a component in the earpieces 102, such as a sensor and/or the speakers 104. For example, the sensor and/or the speakers 104 in the earpieces 102 may be selectively powered when the earpieces 102 are coupled to the body 111 via the connector 114 and connector 108, whereas electronic communication between the sensors and/or the speakers 104 and the chestpiece 110 is discontinued while the earpieces 102 are disconnected from the body 111. In another example, a switch or a proximity sensor may be used to determine whether or not the earpieces 102 are connected based on detecting that the connector 108 has been inserted within connector 114 or based on a distance from the earpieces 102 from the chestpiece 110. In some examples, the CPU 116 may select an operating mode of the dictation stethoscope 100 based on whether the output tube 106 is connected to the chestpiece 110 (e.g., wireless only or wired) in order to adjust operation of the speakers 104 and/or electronic acoustic modifier 120.

In some examples, the chestpiece 110 may include an electrocardiogram (ECG) sensor, which may include two or more electrodes 132 that may be used to obtain ECG signals of the patient 170. The electrodes 132 are physically separated from one another to facilitate measurement of electrical signals on a patient's skin resulting from depolarization of the patient's heart muscle during each heartbeat, when appropriately positioned, e.g., against a patient's chest on the patient's left pectoral region. The chestpiece 110 may include an ADC to digitize voltage differentials measured by electrodes 132, as well as signal processing circuitry to filter and condition the detected signals. ECG signal processing circuitry may be implemented in the analog domain (e.g., prior to digitization), in the digital domain (e.g., by CPU 116 and/or a dedicated digital signal processing integrated circuit), or both. The ECG signals obtained with the electrodes 132 may be sent to external computing device 140 via wireless transceiver 128. The ECG signals may comprise single-lead ECG data. Single-lead ECG data may be obtained from one electrode that may be a ground and another electrode that may be a signal electrode. A voltage difference between the leads may comprise analog ECG signal data. ECG data can be recorded as voltage as a function of time. Alternatively, the ECG data may comprise three-lead ECG data. In still other examples, the ECG data may be obtained via more than three leads (e.g., five-lead ECG data). For example, the ECG electrodes may have between 1 and 12 leads, each capturing different vectors of the electrical polarization of the heart. As such, the ECG electrodes may capture between 1 to 12 different vectors of the electrical polarization of the heart, depending on the number of leads.

In some examples, the chestpiece 110 may include an accelerometer 136. The accelerometer 136 may comprise a three-axis accelerometer, which may provide information about the orientation and motion of the chestpiece 110. The accelerometer 136 may be rigidly affixed to a surface within the chestpiece 110 so that the accelerometer does not move independently from the chestpiece 110 as a whole. The accelerometer may be used to calculate an orientation of the chestpiece 110 when the chestpiece 110 is held stationary by a user. In some examples, the motion (or lack thereof) of the chestpiece 110 measured by the accelerometer 136 may be used to adjust the state of the electronic stethoscope, such as activating/powering on the electronic stethoscope when the accelerometer output indicates that the chestpiece 110 has been picked up by the user or by deactivating/powering off the electronic stethoscope when the accelerometer output indicates the chestpiece 110 has been stationary for a threshold duration. In still further examples, the accelerometer 136 may be used to record seismocardiogram (SCG) data corresponding to lower frequency oscillations (e.g., less than 50 Hz) of the chest wall of the subject and/or the data captured by the accelerometer 136 may be used to determine motion of the patient and/or the chestpiece 110 during recording of the audio and ECG data.

It is to be appreciated that one or more components of the chestpiece 110 shown in FIG. 1B may be located off the chestpiece 110 without departing from the scope of this disclosure. For example, the chestpiece 110 may be communicatively coupled (e.g., acoustically and/or electronically coupled) to a stethoscope device that houses the CPU 116, memory 118, transceiver 128, and/or other electronic components, including the first microphone 122 and/or the second microphone 138 depending the configuration of the chestpiece 110. Further, in some examples, the digital stethoscope may not include the display screen 130, the electrodes 132, and/or the accelerometer 136.

Figure 2:
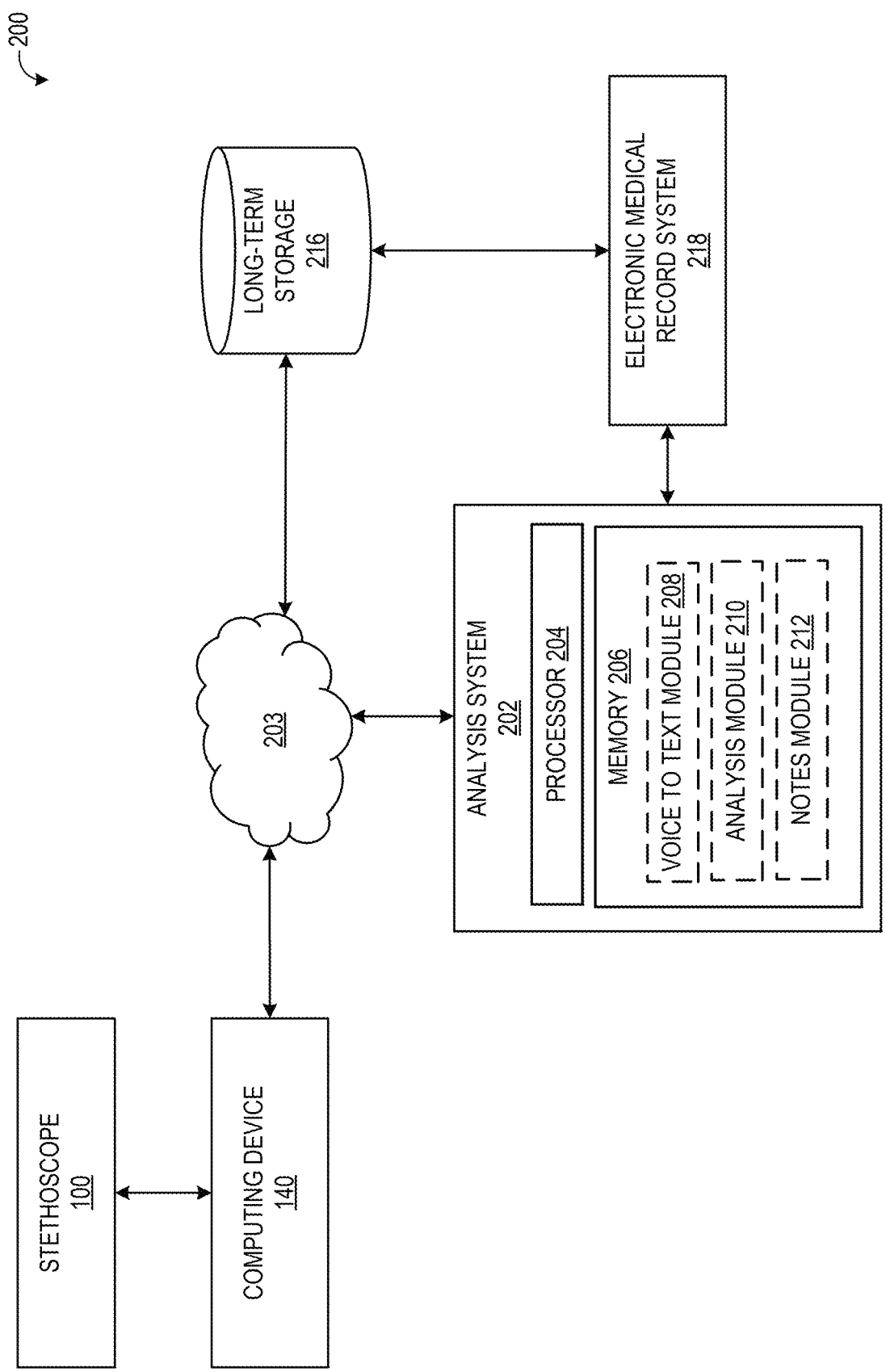
FIG. 2 is a block diagram of a dictation system including the stethoscope of FIGS. 1A and 1B.

FIG. 2 shows a stethoscope dictation system 200 including an analysis system 202 and long-term storage 216, in accordance with one or more embodiments of the disclosure. As explained previously, dictation stethoscope 100 may be employed to capture heart sounds of a patient while operating in a stethoscope mode and capture voice sounds while operating in a dictation mode. The heart sound recordings and voice recordings may be transmitted from the stethoscope 100 to the computing device 140 in real-time (e.g., as the recordings are captured) or at a prescribed frequency. The computing device 140 may then transmit the heart sound recordings (whether the audio files, PCG plots, or both) via a network 203 to the analysis system 202 and/or long-term storage 216.

Analysis system 202 may be communicatively coupled (e.g., via a network, such as network 203) to one or more databases that make up long-term storage 216 as well as computing device 140 (e.g., of FIG. 1A). Computing device 140 is an example computing device and analysis system 202 may be communicatively coupled to a plurality of computing devices that are similar to computing device 140. Computing device 140 may receive heart sound recordings, and in some examples, ECG recordings, of one or more patients from one or more stethoscopes, such as stethoscope 100. Computing device 140 may also receive voice recordings of the one or more patients and/or clinicians from the one or more stethoscopes. At least in some examples, the stethoscopes used to collect the heart sound and voice recordings may be handheld devices that include a first audio sensor (e.g., a first microphone) to capture a heart sound signal and a second audio sensor (e.g., a second microphone) to capture a voice signal, with the first audio sensor and the second audio sensor at least partially encased in a housing of the handheld device and included at fixed positions relative to each other. The heart sound recordings and voice recordings may be saved in long-term storage 216. The stethoscopes may include an ECG sensor (e.g., electrodes).

Analysis system 202 includes a processor 204 configured to execute machine readable instructions stored in non-transitory memory 206. Processor 204 may be single core or multi-core, and the programs executed thereon may be configured for parallel or distributed processing. In some embodiments, processor 204 may optionally include individual components that are distributed throughout two or more devices, which may be remotely located and/or configured for coordinated processing. In some embodiments, one or more aspects of processor 204 may be virtualized and executed by remotely-accessible networked computing devices configured in a cloud computing configuration.

Non-transitory memory 206 may store a voice-to-text module 208, an analysis module 210, and a notes module 212. In some examples, non-transitory memory 206 further stores heart sound recordings, ECG recordings, and voice recordings obtained from the computing device 140. For example, ECG and/or heart sound recordings may be stored (e.g., temporarily) in memory 206 while being processed by analysis module 210 to identify if the ECG and/or heart sound recordings exhibit any clinical findings, as will be explained in more detail below. As another example, voice recordings may be stored (e.g., temporarily) in memory 206 while being processed with voice-to-text module 208, as will also be explained in more detail below.

Voice-to-text module 208 may comprise instructions for automatically generating a text-based voice transcription from a voice recording. However, in some examples, voice-to-text module 208 may be located on computing device 140 and thus voice recordings obtained with stethoscope 100 may be transcribed on computing device 140, and computing device 140 may send text representing the voice recordings (referred to as voice transcriptions) to the analysis system 202 and/or long-term storage 216. Analysis module 210 may include instructions for analyzing heart sound recordings, and when available, ECG recordings (that may be synchronized with the heart sound recordings) to identify clinical findings including patient parameters (e.g., heart rate) and the presence or absence of one or more patient conditions, such as low ejection fraction, murmur, and the like. As such, analysis module 210 may include one or more analysis models each configured to identify the presence or absence of a particular patient condition. The analysis models may be artificial intelligence-based models and/or any other suitable model capable of identifying clinical findings in heart sound recordings. Notes module 212 may include instructions for automatically generating patient notes from the output of the voice-to-text module 208 and analysis module 210. The patient notes may be in the form of subjective, objective, assessment, and plan (SOAP) notes and include indications of the clinical findings determined from the output of the analysis module 210 and selected text segments of the voice transcription output by the voice-to-text module 208. While analysis system 202 and long-term storage 216 are depicted as separate devices/components, it is to be understood that in some examples, analysis system 202 and long-term storage 216 may be included in the same computing system, such as in the same cloud computing system.

In some examples, analysis system 202 and/or long-term storage 216 may be communicatively coupled to an electronic medical record (EMR) system 218. EMR system 218 may be a database stored in a mass storage device configured to communicate with secure channels (e.g., HTTPS and TLS), and store data in encrypted form. Further, the EMR system 218 may be configured to control access to patient electronic medical records such that only authorized healthcare providers may edit and access the electronic medical records. An EMR for a patient may include patient demographic information, family medical history, past medical history, lifestyle information, preexisting medical conditions, current medications, allergies, surgical history, past medical screenings and procedures, past hospitalizations and visits, etc. EMR system 218 may be located at a medical facility or may be part of a distributed (e.g., cloud) computing system.

Figure 3:
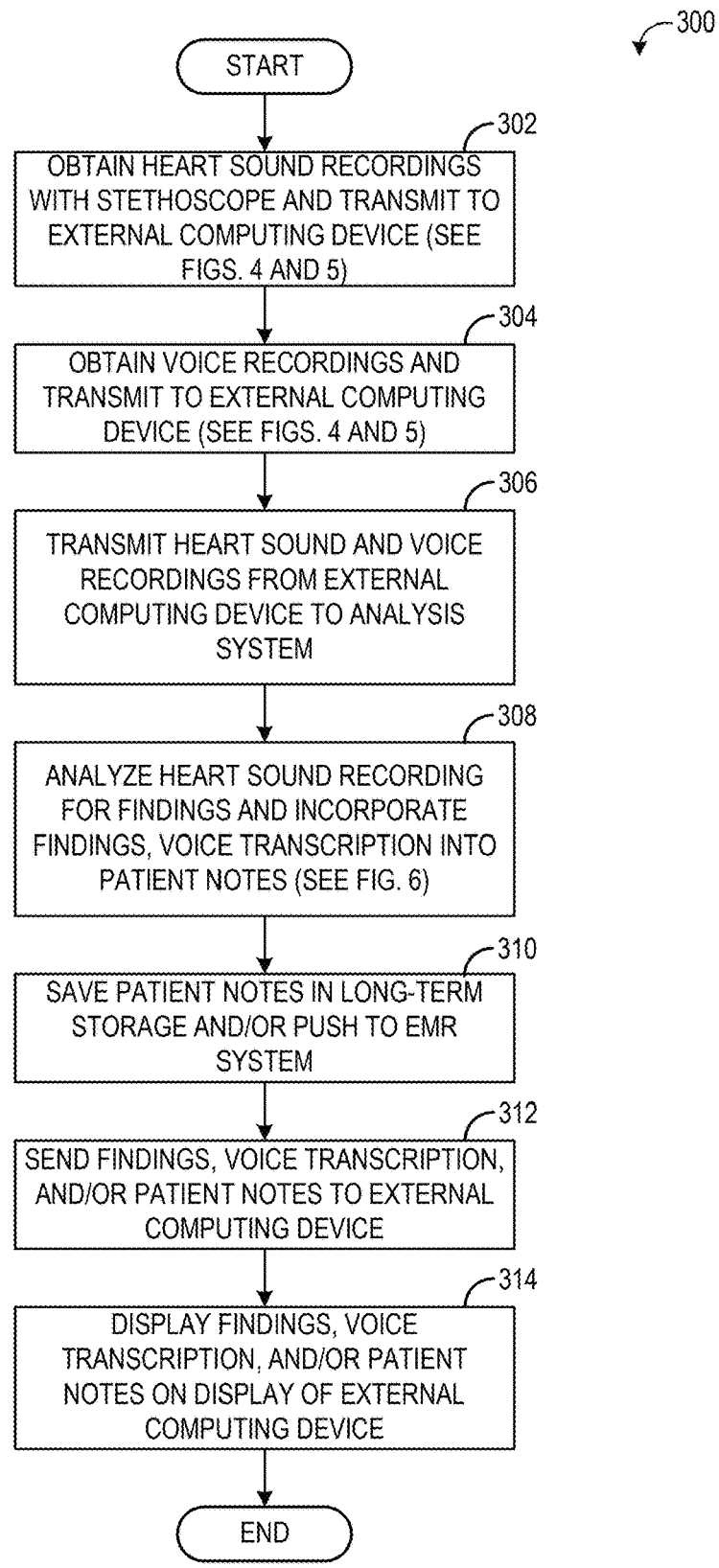
FIG. 3 is a high-level flow chart illustrating an example method for medical dictation using a dictation stethoscope.

FIG. 3 is a flow chart illustrating a method 300 for obtaining, processing, and storing voice recordings with a dictation stethoscope, such as dictation stethoscope 100 of FIGS. 1A-2. Method 300 may be implemented by the system shown in FIG. 2, though other systems are possible without departing from the scope of this disclosure.

At 302, a heart sound recording is obtained with the dictation stethoscope (e.g., when operating in a stethoscope mode) and transmitted to an external computing device, such as external computing device 140. At 304, a voice recording is obtained with the digital stethoscope (e.g., when operating in a dictation mode) and transmitted to the external computing device. Additional details about obtaining heart sound recordings and voice recordings are presented below with respect to FIGS. 4 and 5. Briefly, as explained below with respect to FIG. 4, a first microphone of the dictation stethoscope may be used to obtain the heart sound recording during a stethoscope mode, and ambient recordings captured with a second microphone of the dictation stethoscope may be used for noise cancellation to improve the quality of the heart sound recording. During a dictation mode, no audio may be captured with the first microphone, and the second microphone may be used to capture voice recordings. As explained below with respect to FIG. 5, in some examples, the dictation stethoscope may include an array of second microphones and beamforming may be performed to improve the quality of the voice recordings and/or allow for ambient scribing, where voice recordings of multiple people may be captured. In some examples, during capture of the heart sound recording, an ECG recording may also be captured. Further, it is to be appreciated that while method 300 (as well as methods 400 and 500 described below with respect to FIGS. 4 and 5) is described as capturing heart sound recordings during the stethoscope mode, it is to be appreciated that other physiological sounds could be captured during the stethoscope mode, such as lung sounds.

In some examples, the heart sound recording may be transmitted in real-time or substantially real-time relative to capturing of the heart sound recording. For example, the heart sound recording may be transmitted as the heart sound recording is captured (e.g., a first segment of the heart sound recording, such as a segment of 0.1-1.0 seconds, may be transmitted to the external computing device while one or more additional segments of the heart sound recording are still being captured), such that the heart sound recording is transmitted to the external computing device within 1 second of being captured. Similarly, the voice recording may be transmitted in real-time or substantially real-time relative to capturing of the voice recording. In such examples, the voice recording may not be stored locally on the dictation stethoscope. However, real-time transmission of the voice recording may result in increased battery usage, due to the relatively long time duration that the voice recording may span (e.g., a typical voice recording may be in the range of 30 seconds to 10 minutes, with some voice recordings lasting upwards of 20-30 minutes or longer). Thus, in some examples, each voice recording may be stored locally on the dictation stethoscope until the capturing of that voice recordings is terminated, at which point the entirety of the voice recording may be transmitted to the external computing device at once, which may reduce battery consumption. After transmitting the voice recording to the external computing device, the voice recording may be deleted from the dictation stethoscope.

It is to be appreciated that the heart sound recording and the voice recording may be transmitted to the external computing device separately (e.g., the heart sound recording may not be transmitted at the same time the voice recording is transmitted), but may be transmitted using the same transmission interface, such as via the wireless transceiver 128 using the wireless transmission protocol (e.g., Bluetooth LE Audio). Further, in some examples, the heart sound recording may be projected from one or more speakers, such as speaker(s) 104.

At 306, the heart sound and voice recordings received at the external computing device are transmitted to a remote analysis system, such as analysis system 202 of FIG. 2. If an ECG recordings was captured, the ECG recording may also be transmitted to the analysis system. In some examples, the heart sound recording and/or the voice recording may undergo processing at the external computing device prior to being transmitted to the analysis system. For example, the signal quality of the heart sound recording may be determined at the external computing device and the heart sound recording may be transmitted to the analysis system only if the heart sound recording has a signal quality above a threshold. In some examples, the external computing device may create a PCG representation for the heart sound recording and display the PCG representation on a display screen of the external computing device. In some examples, the external computing device may include a voice-to-text module configured to create a text-based voice transcription of the voice recording to be sent to the analysis system. In other examples, the voice-to-text module may reside on the analysis system.

At 308, method 300 includes analyzing, with the analysis system, the heart sound recording for clinical findings and incorporating the clinical findings and a voice transcription of the voice recording into patient notes. Additional details about analyzing the heart sound recording (and, when included, ECG recoding) for clinical findings and incorporation of the clinical findings and voice transcription of the voice recording into patient notes are provided below with respect to FIG. 6. The patient notes may be formatted in a suitable manner and include portions of the text extracted from the voice transcription, or may include the entirety of the voice transcription.

At 310, the patient notes are saved in long-term storage and/or pushed to an EMR system. The long-term storage, such as long-term storage 216, may include one more mass storage devices configured to store the patient notes along with the clinical findings, the heart sound audio recording, the PCG of the heart sound recording, the ECG recording (if included), and/or the voice transcription in a patient file (such that any previous clinical findings, heart sound recordings, patient notes, etc., for the patient are associated with the current patient notes) that is accessible to one or more users (e.g., clinicians) for subsequent review. The analysis system may additionally or alternatively push the patient notes (and, in some examples, the PCG, ECG, etc.) to the EMR system, such as EMR system 218, so that the patient notes can be saved as part of the patient's EMRs and available for later review by one or more users.

Figure 7:
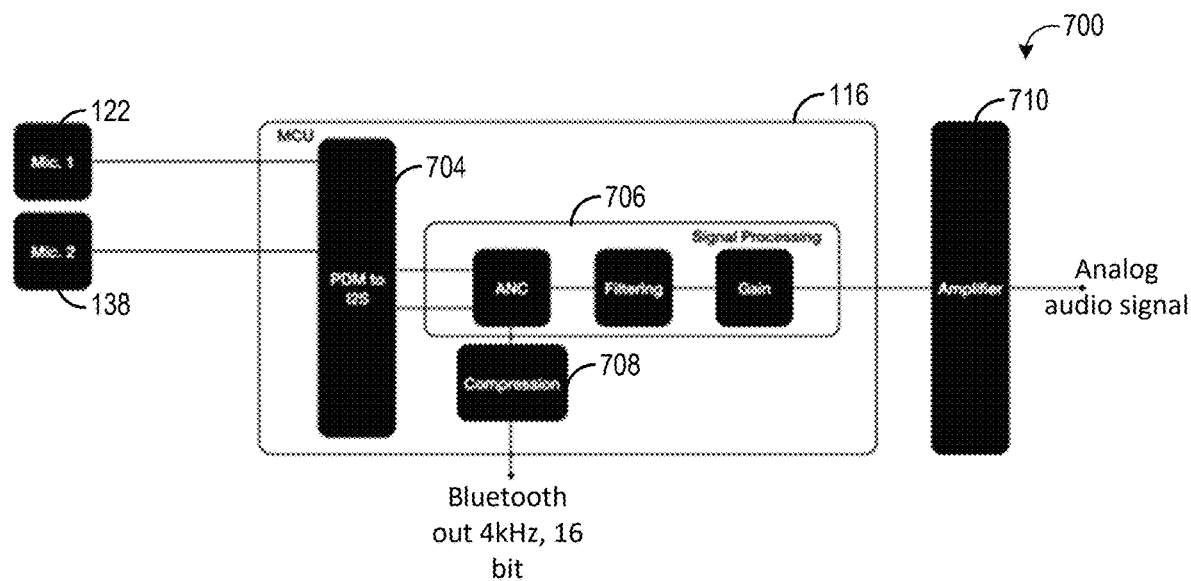
FIGS. 7 and 8 show example processing pipelines that may be employed by the stethoscope of FIGS. 1A-2.

At 312, the clinical findings, voice transcription, and/or patient notes may be sent from the analysis system to the external computing device, where the clinical findings, voice transcription, and/or patient notes may be displayed on the display screen of the external computing device, as indicated at 314. An example display screen of the external computing device displaying clinical findings, voice transcription, and/or patient notes is shown in FIG. 7 and described in more detail below. Method 300 then ends.

It is to be appreciated that in some instances, method 300 may be executed without obtaining heart sound recordings. For example, some patient encounters may not involve auscultation with the dictation stethoscope, but the practitioner examining the patient may still wish to use the dictation stethoscope in the dictation mode to obtain voice recordings of the patient encounter. In such examples, the voice transcription may be incorporated into patient notes and/or saved in long-term storage without inclusion of any clinical findings based on the heart sound recordings.

Figure 4:
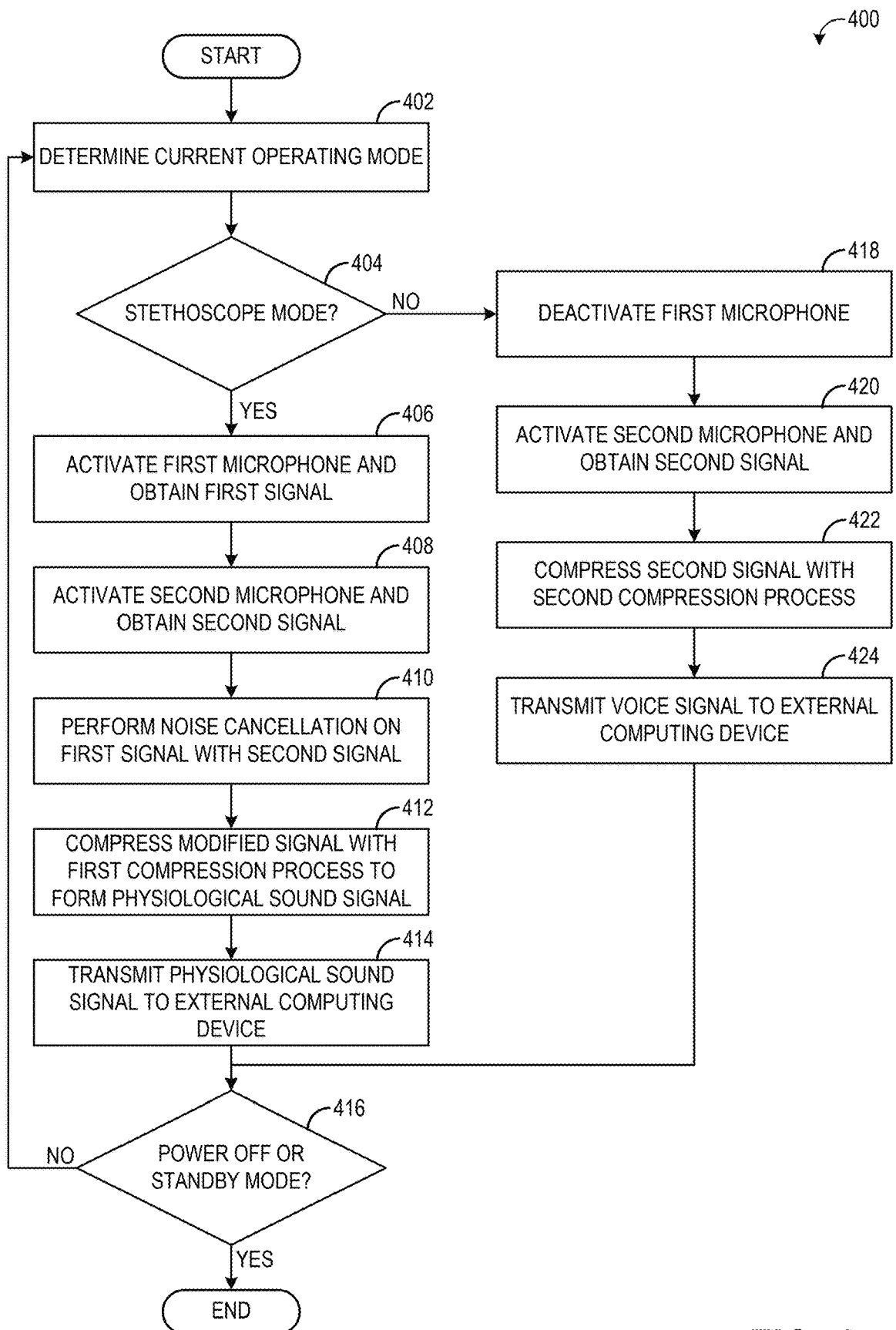
FIG. 4 is a flow chart illustrating an example method for operating the dictation stethoscope during the medical dictation of FIG. 3.

FIG. 4 illustrates a method 400 for operating a dictation stethoscope, such as dictation stethoscope 100 of FIGS. 1A-2. Method 400 may be carried out according to instructions stored in memory of the dictation stethoscope, such as memory 118, and executed via one or more processors of the dictation stethoscope, such as processor(s) within CPU 116.

At 402, method 400 includes determining the current operating mode of the dictation stethoscope. The dictation stethoscope may be configured to operate in a stethoscope mode or in a dictation mode, as explained previously. The dictation stethoscope may have a default operating status that the dictation stethoscope may be operated in when the dictation stethoscope is initially powered on. In some examples, the default operating status may be the stethoscope mode and the dictation stethoscope may only operate in the dictation mode in response to a user input requesting the dictation stethoscope operate in the dictation mode. The user input may include user selection of a dictation button on the dictation stethoscope (e.g., the button of the one or more user input devices 134) or a voice command from the user instructing the dictation stethoscope to operate in the dictation mode. For example, the dictation stethoscope may monitor output from the external microphone (e.g., the second microphone) to determine if the voice command instructing to operate in the dictation mode has been received. The monitoring for the voice command may be carried out either by the microprocessor/CPU of the dictation stethoscope in a low power state (e.g., without all functionality operational) or carried out at the microphone. The monitoring for the voice command may be carried out in parallel to the noise canceling while in stethoscope mode, e.g., the audio data captured by the second microphone can be sent from the second microphone to both the noise canceling and the voice command detection components of the digital signal processing of the microprocessor.

Thus, upon powering on of the dictation stethoscope, the dictation stethoscope may operate in the stethoscope mode until a user input is received instructing the dictation stethoscope to operate in the dictation mode. If the dictation stethoscope is already operating in the dictation mode (as will be explained in more detail below), the dictation stethoscope may remain in the dictation mode until the stethoscope is powered down or until a user input is received instructing the dictation stethoscope to enter a standby mode or switch to the stethoscope mode. Switching to the stethoscope mode may be performed in response to detection of fingers on the chestpiece of the dictation stethoscope using touch sensors (e.g., the touch sensor(s) of the one or more user input devices 134), detection of heart sounds in the audio captured by a first microphone of the dictation stethoscope, or detection of an earpiece of the dictation stethoscope being placed into an ear of a user, which may be based on output from optical/light sensor(s) positioned at the earpiece(s) (e.g., as the optical/light sensor may detect when the earpiece is occluded by an ear canal of the user). In still further examples, the button that may be selected to enter into the dictation mode may be a toggle button that can be actuated to a first position to enter the dictation mode and to a second position to enter the stethoscope mode.

At 404, method 400 includes determining if the current operating mode of the dictation stethoscope is the stethoscope mode. If the current operating mode is the stethoscope mode, method 400 proceeds to 406 to activate the first microphone (if not already activated) and obtain a first signal output by the first microphone. For example, the first microphone (e.g., the first microphone 122) may be configured to translate vibrations received at the first microphone (e.g., due to movement of a diaphragm that in turn moves a volume of air inside the chestpiece) into a voltage signal that is digitized by an ADC to create the first signal. At 408, method 400 includes activating a second microphone (if not already activated) of the dictation stethoscope and obtaining a second signal output by the second microphone. For example, the second microphone (e.g., the second microphone 138) may be configured to translate vibrations received at the second microphone (e.g., due to ambient sounds, as the second microphone may face the environment) into a voltage signal that is digitized by an ADC to create the second signal.

The first signal may be modified to form a physiological sound signal. For example, at 410, noise cancellation may be performed on the first signal using the second signal to form a modified first signal. For example, an amplitude of the noise component from the first signal may be reduced or removed based on the second signal to improve the quality of the first signal. At 412, the modified first signal is compressed with a first compression process, such as a lossless compression process (e.g., adaptive differential pulse-code modulation (ADPCM)) to form the physiological sound signal. The resultant physiological sound signal (which may be a heart sound recording, in the form of a WAV file or another suitable audio file) is transmitted to an external computing device (e.g., external computing device 140) at 414, as explained above with respect to FIG. 3. The physiological sound signal may be downsampled prior to compression and transmission to a first sampling rate, which may be relatively low, such as 4000 samples/s (e.g., 4000 Hz). If the dictation stethoscope includes ECG electrodes, an ECG signal may also be obtained while the first signal is obtained, and the ECG signal may also be transmitted to the external computing device.

At 416, method 400 may determine if the dictation stethoscope has been powered off or entered into a standby mode. The dictation stethoscope may be powered off in response to a user actuating a power button of the dictation stethoscope. The dictation stethoscope may be entered into the standby mode in response to determining that heart sounds (or lung sounds, etc.) are not being captured with the first microphone and have not been captured for a prior duration of time (e.g., five seconds, ten seconds) and in response to determining that the dictation stethoscope is not operating in the dictation mode. In the standby mode, the dictation stethoscope may not capture signals with the microphones and may power down certain components of the dictation stethoscope, such as a display screen, to conserve battery life, but the dictation stethoscope may still be powered on. If the dictation stethoscope has been powered off or has entered standby mode, method 400 ends. If the dictation stethoscope has not been powered off and has not entered standby mode, method 400 proceeds to 402 to continue to determine the current operating mode. If the dictation stethoscope is still in the stethoscope mode, the first signal from the first microphone continues to be captured and digitized, with the second signal from the second microphone used for noise cancellation.

However, at 404, if it is determined that the stethoscope is not operating in the stethoscope mode, the stethoscope is thereby operating in the dictation mode and method 400 proceeds to 418 to deactivate the first microphone (if activated). At 420, method 400 includes activating the second microphone (or maintaining the second microphone in the activated state) and obtaining the second signal output by the second microphone.

The second signal may be processed to form a voice signal. The processing may include filtering in some examples. Further, the processing may include, at 422, compressing the second signal using a second compression process that is different than the first compression process, such as a lossy compression process. For example, a lossy audio codec may be used to reduce the size of data to be transmitted. The lossy codec may be optimized for relatively low sample frequency voice signals. The second compression process may reduce the size of the resultant audio file to facilitate wireless transmission but may retain information for enabling an accurate voice transcription to be made from the voice signal. The resultant voice signal (which may be a voice recording, in the form of an MP3 file or another suitable audio file) is transmitted to the external computing device at 424, as explained above with respect to FIG. 3. In some examples, the voice signal is not downsampled and thus has a second sampling rate that may be relatively high, such as higher than the first sampling rate. In some examples, the second sampling rate may be 8000 Hz.

Method 400 then proceeds to 416 to determine if the dictation stethoscope has been powered off or entered into standby mode, and if not, loop back to 402 to determine the current operating mode of the dictation stethoscope.

Thus, the dictation stethoscope may be operated in a stethoscope mode or in a dictation mode based on user input. When in the stethoscope mode, the two microphones of the dictation stethoscope may be used to capture a high-quality heart sound recording, with the first microphone of the dictation stethoscope used to capture the heart sounds (owing to the location of the first microphone in the dictation stethoscope) and the second microphone used to capture ambient sounds for noise cancellation. The sampling rate of the two microphones during the stethoscope mode may be relatively low, which may reduce battery consumption of the dictation stethoscope and result in collection of heart sound recordings that match heart sound recordings obtained with conventional electronic/digital stethoscopes. The modified first signal (e.g., the signal captured by the first microphone after noise cancellation) may be compressed with a lossless compression process, which may retain all information in the heart sound recording that may be demanded for accurate analysis of the heart sound recording. Further, lossy compression methods rely on codecs that are not specifically configured for physiological sounds and thus using lossless compression prevents removal of information from the first (e.g., physiological sound) signal that may occur using lossy compression. When in dictation mode, the first microphone may be ignored (e.g., deactivated or its output simply discarded) and the second microphone may be used to capture a voice recording. The sampling rate of the second microphone during the dictation mode may be relatively high, which may allow accurate capture of the frequency/amplitude spectrum associated with human voice sounds. The second signal of the second microphone may be compressed with a lossy compression process, which may reduce the file size for transmission off the dictation stethoscope while retaining information demanded for voice-to-text transcription, as codecs for lossy compression are configured based on human perception of voice sounds.

Figure 5:
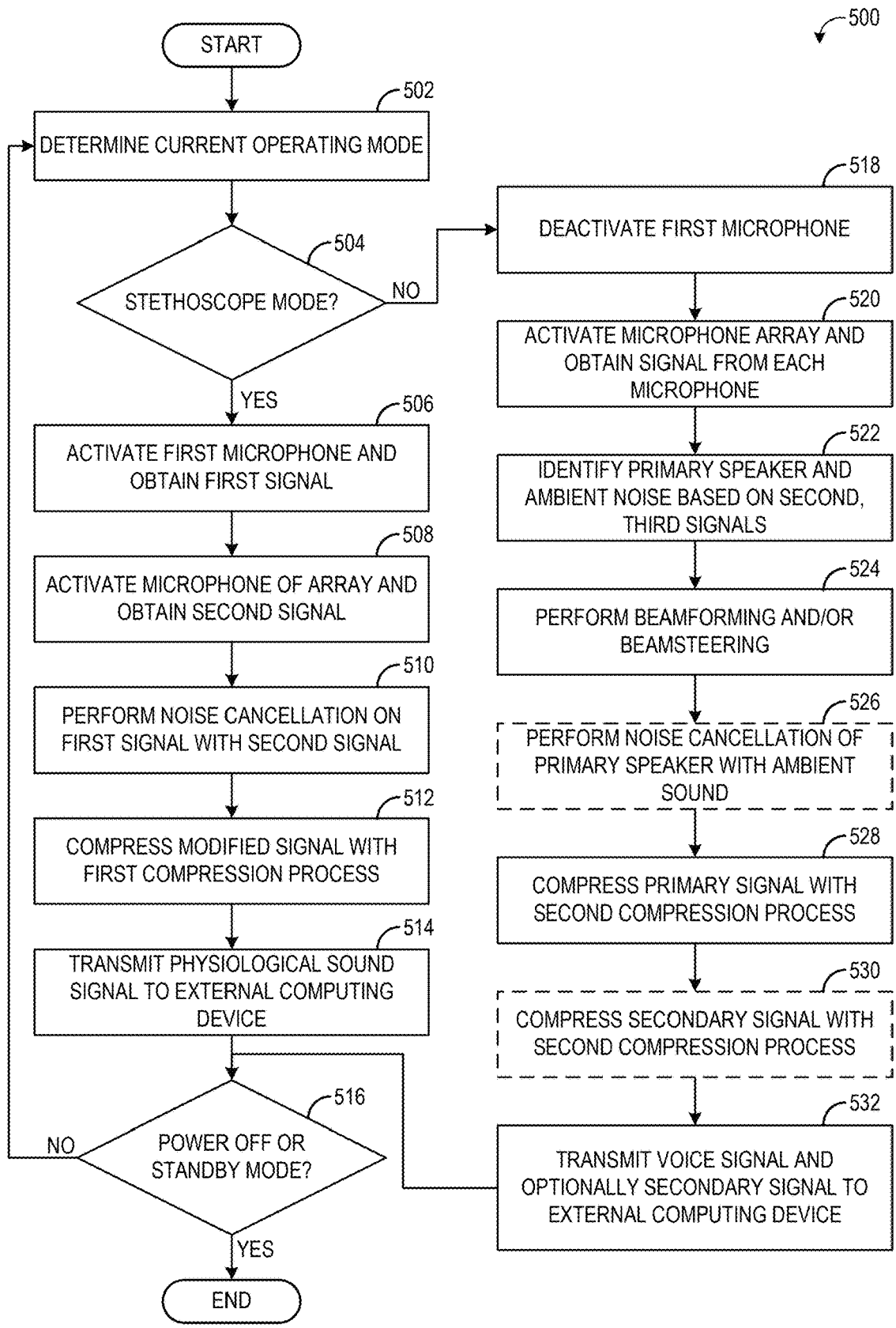
FIG. 5 is a flow chart illustrating another example method for operating the dictation stethoscope during the medical dictation of FIG. 3.

FIG. 5 illustrates a method 500 for operating a dictation stethoscope, such as dictation stethoscope 100 of FIGS. 1A-2. Method 500 may be carried out according to instructions stored in memory of the dictation stethoscope, such as memory 118, and executed via one or more processors of the dictation stethoscope, such as processor(s) within CPU 116. Method 500 may be similar to method 400, but may be implemented in a dictation stethoscope that includes an array of second microphones, rather than a single second microphone. Thus, some of the operations of method 500 may be similar to corresponding operations of method 400, and description of those operations provided in method 400 likewise applies to method 500.

At 502, method 500 includes determining the current operating mode of the dictation stethoscope, and at 504, method 500 determines if the dictation stethoscope is currently operating in the stethoscope mode. Determining the current operating mode may be performed in the same manner as described above with respect to FIG. 4, and thus the description provided for operations 402 and 404 of method 400 likewise apply to operations 502 and 504 of method 500. At 506, method 500 includes activating the first microphone and obtaining the first signal at the first sampling rate (e.g., 4000 Hz), as explained above with respect to 406 of method 400.

At 508, method 500 includes activating one or more microphones of the array of second microphones and obtaining a second signal (and optionally one or more additional signals) from the one or more microphones of the array. In some examples, only one microphone of the array of second microphones may be activated in order to capture one second signal for noise cancellation.

At 510, noise cancellation is performed on the first signal using the second signal to form a modified first signal, and the modified first signal is compressed using the first compression process to form the physiological sound signal, which may be performed similarly to operations 410 and 412 of method 400, respectively. At 514, the physiological sound signal is transmitted to the external computing device, as explained above with respect to operation 414 of method 400. At 516, method 500 includes determining if the dictation stethoscope has been powered off or entered into standby mode, as explained above with respect to operation 416 of method 400. If the dictation stethoscope has been powered off or has entered standby mode, method 500 ends. If the dictation stethoscope has not been powered off and has not entered standby mode, method 500 proceeds to 502 to continue to determine the current operating mode. If the dictation stethoscope is still in the stethoscope mode, the first signal from the first microphone continues to be captured and processed, with the second signal from the one or more microphones of the array used for noise cancellation.

However, at 504, if it is determined that the stethoscope is not operating in the stethoscope mode, the stethoscope is thereby operating in the dictation mode and method 500 proceeds to 518 to deactivate the first microphone (if activated). At 520, method 500 includes activating the array of second microphones and obtaining a signal from each microphone of the array (e.g., where each signal is output by a respective microphone of the array). For example, a second signal may be obtained from a first microphone of the array, a third signal may be obtained from a second microphone of the array, etc. At 522, method 500 includes identifying a primary speaker and ambient noise in the environment surrounding the dictation stethoscope based on the second signal, the third signal, and any other signals from the array. The primary speaker may be the source of sound that is closest to the array of second microphones and/or has the highest amplitude, or otherwise displays characteristics associated with human voice rather than ambient noise. The angle of incidence of sound, as determined from the signals from the array, can be used to identify the primary speaker and ambient sound.

At 524, beamforming and/or beamsteering may be performed. Beamforming may include using the microphones of the array to produce a directional response which is more sensitive at specific angles than others. Beamforming may be performed to produce the directional response that is more sensitive at the angle of sound corresponding to the primary speaker relative to other angles. Beamsteering may include adjusting the angle of the "beams" (e.g., received sound beams) to improve signal to noise ratio. For example, time delays may be added to one or more of the second signals, and the time-delayed second signals may be compounded to form one "beam" that is sensitive at the angle of sound corresponding to the primary speaker.

For example, beamforming may be used to identify the direction of the speaker (voice source) relative to the microphone array. This information can then be used to adjust the processing of the microphone signals, such as by applying adaptive filtering techniques to enhance the desired voice signal and reduce the impact of background noise or interference from other sound sources, including noise generated by the stethoscope sliding along clothing or a person's body. By accurately locating the position of the speaking source (e.g., the practitioner's mouth location relative to the stethoscope), the system can better focus on the relevant audio signals, leading to improved voice recognition, speech enhancement, and overall performance in voice-based applications.

The beamforming for voice detection may be based on several factors, including the number and placement of the microphones, the compensation by time delay and phase shift calculations, and the specific acoustic environment in which the system is operating (e.g., a quiet examination room or a noisy emergency room).

One example beamforming approach that can be used for voice detection and localization is the delay-and-sum beamforming technique. In delay-and-sum beamforming, the system applies appropriate time delays to the signals from each microphone in the array, and then sums the delayed signals to create a directional beam. The time delays are calculated based on the assumed direction of the sound source and the geometry of the microphone array.

For a linear microphone array with N microphones, the delay-and-sum beamforming process may include capture of the audio signals from the N microphones in the array, denoted as x1(t), x2(t), ..., xN(t), where t represents the time domain. The time delays $\tau 1, \tau 2, \ldots, \tau N$ that would be required to align the signals from each microphone may be calculated, assuming the sound source is located at a specific direction ($\theta, \varphi$) relative to the array. The time delays are determined based on the distances between each microphone and the assumed sound source location. The calculated time delays are applied to the individual microphone signals:

$$y1(t)=x1(t-\tau 1)$$

$$y2(t)=x2(t-\tau 2)$$

$$\ldots$$

$$yN(t)=xN(t-\tau N)$$

Finally, the delayed signals are summed to create the beamformed output:

$$z(t)=y1(t)+y2(t)+\ldots+yN(t)$$

The beamformed output z(t) may have a stronger signal-to-noise ratio (SNR) in the direction of the assumed sound source, as the time delays align the desired signal components while the undesired signals (e.g., noise, interference) are partially canceled out.

To detect the position of the sound source, the beamforming process can be repeated for different assumed directions ($\theta, \varphi$), and the direction that produces the maximum beamformed output power can be considered the estimated location of the sound source. Additionally, more advanced beamforming techniques, such as adaptive beamforming or spatial filtering, may be used if desired. An alternative method of differential beamforming may also be used where the signal at the first microphone of the array is summed with an inverted and delayed signal from the other microphones in the array. This can be applied to an N microphone array where the signal at each microphone is x1(t), x2(t), ..., xN(t). The directivity pattern will be a function of the spacing of the microphones and the delay applied to each microphone signal. For a cardioid pattern with high attenuation behind the array, the delay (for each of the other microphones in the array) will match the time taken for the sound wave to travel the distance between that microphone and the first microphone in the array. Time delays are applied to the signals: y1(t)=x1(t), y2(t)=x2(t-τ2), ..., yN(t)=xN(t-τN). Finally, the inverted signals are summed with the first signal in the array: z(t)=y1(t)-y2(t)- ... -yN(t). In this way, the beamforming may be performed in part based on the specific positioning of the microphones in the array (e.g., the distance between each microphone).

At 526, method 500 optionally includes performing noise cancellation of the sounds corresponding to the primary speaker (which may be referred to as the primary signal) with the sounds corresponding to the ambient sound (which may be referred to as the secondary signal). At 528, the primary signal is compressed with the second compression process (e.g., the lossy compression described above with respect to FIG. 4) to form a voice signal. At 530, method 500 optionally includes compressing the secondary signal with the second compression process. At 532, method 500 includes transmitting the voice signal and optionally the compressed secondary signal to the external computing device at the second sampling rate (e.g., 8000 Hz). If the secondary signal is compressed and transmitted to the external computing device, additional speakers in the environment beyond the primary speaker may be captured, so that the patient, other practitioners, etc., may be recorded, which may be referred to as ambient scribing. Method 500 then proceeds to 516 to determine if the dictation stethoscope has been powered off or entered into standby mode, and if not, loop back to 502 to determine the current operating mode of the dictation stethoscope.

Figure 6:
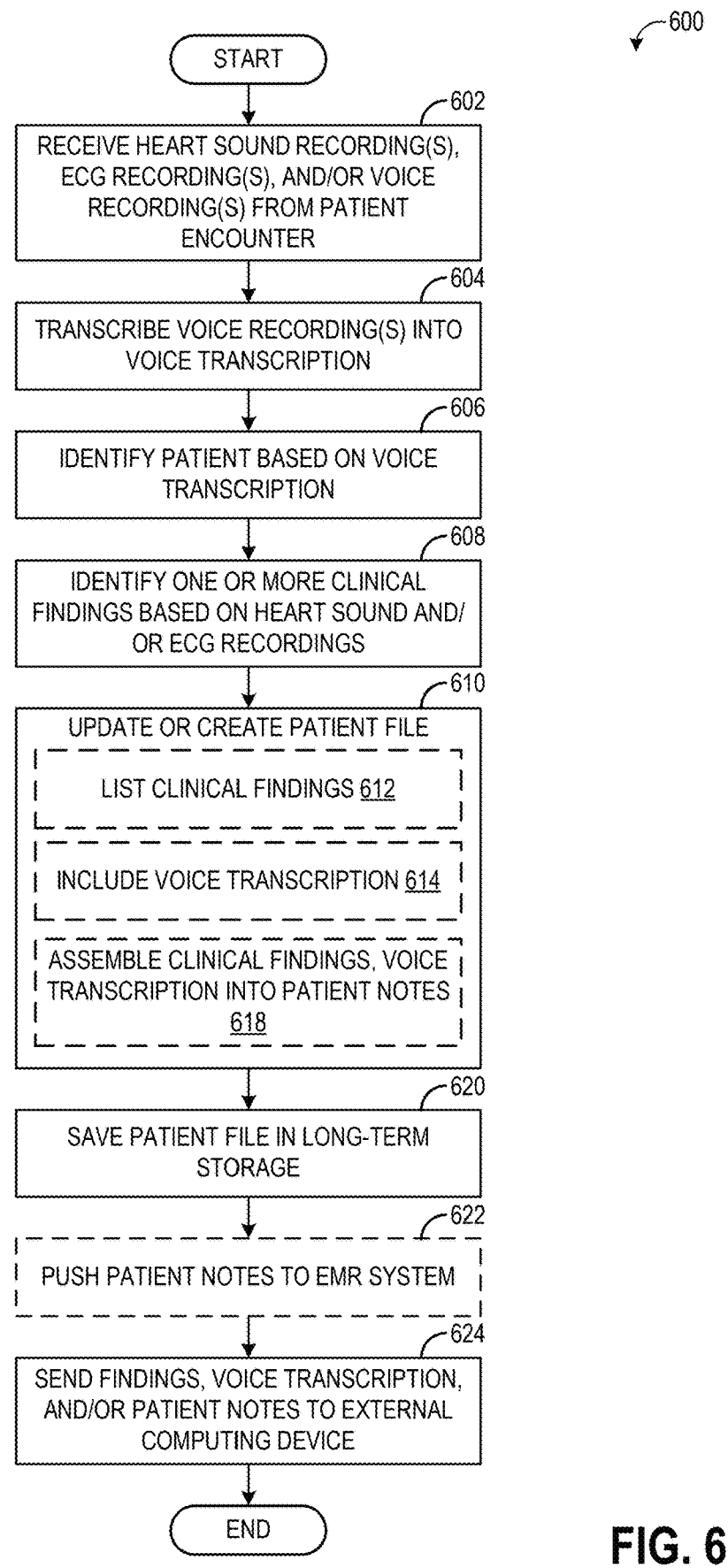
FIG. 6 is a flow chart illustrating a method for integrating voice transcriptions generated from the medical dictation into patient notes.

FIG. 6 illustrates a method 600 for processing heart sound recordings and/or voice recordings with an analysis system, such as analysis system 202 of FIG. 2. Method 600 may be carried out according to instructions stored in memory of the analysis system, such as memory 206, and executed via one or more processors of the analysis system, such as processor 204. It is to be appreciated that FIG. 6 is described with respect to heart sound recordings, but any other physiological sound recordings could be captured and processed as described below (e.g., lung sounds).

At 602, method 600 includes receiving heart sound recording(s), ECG recording(s), and/or voice recording(s) collected during a patient encounter. The patient encounter may include an exam/visit with a patient and a practitioner. The heart sound recording(s), ECG recording(s), and/or voice recording(s) may be captured with a dictation stethoscope (e.g., dictation stethoscope 100) operated by the practitioner and sent from the dictation stethoscope to an external computing device (e.g., external computing device 140) before being sent to the analysis system, as explained above with respect to FIGS. 3-5.

At 604, method 600 may include transcribing the voice recording(s) into a voice transcription. For example, the voice-to-text module 208 may be invoked to generate the voice transcription from the voice recording(s) of the patient encounter. However, in other examples, the external computing device may perform the transcription and the analysis system may receive the voice transcription of the voice recording(s) from the external computing device. The voice recording(s) may include multiple recordings, such as a recording of a primary speaker and a recording of ambient sounds, or multiple recordings taken at different time segments. The voice transcription may stitch together the separate voice recordings based on a time-stamp of each voice recording, for example.

At 606, method 600 includes identifying the patient being examined in the patient encounter based on the voice transcription. In some examples, while speaking during the dictation mode, the practitioner may identify the patient by name and/or medical record number. The analysis system may be configured to identify the patient from the voice transcription by identifying a trigger word or phrase (e.g., "patient name" or "patient number") and then extracting the patient identity from the word(s) that follows the trigger word or phrase. In some examples, the practitioner may be instructed (e.g., via instructions output on/by the external computing device or the dictation stethoscope) to identify the patient when commencing the dictation mode.

At 608, method 600 includes identifying one or more clinical findings based on the heart sound and/or ECG recordings. As explained above with respect to FIG. 2, the analysis system may include an analysis module 210 configured to identify clinical findings by invoking one or more analysis models configured to process the heart sound and/or ECG recordings to determine a presence or absence of a respective patient condition (e.g., low ejection fraction, murmur, stenosis, etc.). The analysis module may be further configured to calculate or infer various patient parameters from the heart sound and/or ECG recordings, such as heart rate, pulmonary artery pressure, and so forth. In this way, the clinical findings may include patient parameters (e.g., heart rate) and/or patient conditions (e.g., presence or absence of low ejection fraction, murmur, etc.). In some examples, the voice transcription may be used to identify certain characteristics of the patient, for example whether the patient is an adult or a child, or the age of a patient or the weight of a patient. This information may be used by the analysis module to improve the accuracy of the heart sound/ECG analysis.

At 610, method 600 includes updating or creating a patient file for the patient. When the patient is identified at 606, the analysis system may determine if a file exists for the patient (e.g., wherein the file is a collection of stored data associated with the patient that is stored in the analysis system and/or long-term storage). If a file does not already exist, the analysis system may automatically create a new file for the patient. If a file does exist, the analysis may update the file for the patient. The patient file may include the heart sound recording, ECG recording (e.g., one or more ECG plots each corresponding to an ECG lead), and/or PCG plot that represents the heart sound recording. The analysis system may be configured to associate the heart sound recording, ECG recording, and/or PCG plot with the patient due to the proximity in time of the heart sound recording and ECG recording relative to the voice recording. For example, the heart sound recording, ECG recording, and voice recording may each be time-stamped and device-stamped (e.g., metadata for each of the heart sound recording, ECG recording, and voice recording may identify the dictation stethoscope used to collect the heart sound recording, ECG recording, and voice recording) and the analysis system may associate the heart sound recording and ECG recording with the voice recording and hence the patient (e.g., based on identifying the patient from the voice transcription of the voice recording) based on the fact that the heart sound, ECG, and voice recordings were all obtained from the same dictation stethoscope and within a threshold time range of each other.

As indicated at 612, the new or updated patient file for the patient may include a list of the clinical findings identified at 608. The clinical findings may be summarized in a note for each clinical finding that identifies the clinical finding and includes any additional information about the clinical finding. Further, as indicated at 614, creating or updating the patient file may include saving the voice transcription as part of the patient file. In some examples, an entirety of the voice transcription may be included in the patient file. In other examples, only a portion of the voice transcription may be included in the patient file. At 618, updating or creating the patient file may further include assembling the clinical findings and at least parts of the voice transcription into patient summary notes (also referred to herein as patient notes). The patient notes may be formatted in a suitable manner and may be created using a notes module of the analysis system (e.g., notes module 212). In some examples, the patient notes may be in the form of SOAP notes. The clinical findings (and specifically the notes for each finding) may be included in the objective and/or assessment components of the SOAP notes and the analysis system may be configured to extract relevant parts of the voice transcription to include in the subjective, objective, assessment, and/or plan components. Additionally, the patient notes may include patient identification information (e.g., name and/or MRN) as determined from the voice transcription. Additionally or alternatively, the patient notes may include practitioner identification information (e.g., name), which may be determined from the voice transcription (e.g., the practitioner may state their name when the voice recording is captured) or from the metadata sent with the heart sound, ECG, and/or voice recordings (e.g., wherein the metadata identifies the dictation stethoscope and the analysis system stores pairings between dictation stethoscopes and practitioners).

At 620, method 600 includes saving the patient file in long-term storage, such as long-term storage 216. As explained above, the patient file may include the clinical findings determined by the analysis module and a portion or an entirety of the voice transcription of the voice recording(s). The patient file may additionally include the heart sound recording(s) (both the audio file and PCG representation), ECG recording(s), and/or voice recording(s), which may allow for users (e.g., the practitioner) to listen to the heart sound recording(s) and/or voice recording(s), if desired, as well as view the PCG representation(s) of the heart sound recording(s) and the ECG recording(s).

At 622, method 600 optionally includes pushing the patient notes to an EMR system, such as EMR system 218. The EMR system may store one or more record for each patient encounter, where the records include patient vital signs recorded during each patient encounter, clinical notes entered by the practitioner for each patient encounter, and the like. The analysis system may be communicatively coupled to the EMR system and configured to automatically send the patient notes to the EMR system so that the patient notes can be saved as part of the patient's medical records. In this way, the practitioner may avoid interacting with the EMR system but still be able to save a record of the patient encounter.

At 624, method 600 includes sending the clinical findings, voice transcription (or a portion of the voice transcription), and/or patient notes to the external computing device. The external computing device may in turn display the clinical findings, voice transcription, and/or patient notes on the display screen of the external computing device for review by the practitioner.

It is to be appreciated that the clinical findings (as well as a PCG plot and/or ECG plot(s)) may be displayed on the display screen of the external computing device prior to or during acquisition of the voice recording. For example, the practitioner may perform auscultation on the patient and the heart sound and ECG recordings may be sent to the analysis system for identification of clinical findings. While the analysis models are executing in order to identify any clinical findings, the display screen of the external computing device may display a graphical user interface (GUI) that includes the PCG and ECG plots and an indication that analysis of the heart sound and ECG recordings is in process. The GUI may be updated once the analysis models are done executing and the clinical findings are sent to the external computing device, with the updated GUI showing the results of the analysis models (e.g., whether or not any abnormalities were identified). At that point or thereafter, the practitioner may initiate operation of the dictation stethoscope in the dictation mode to capture a voice recording that identifies the patient, the reason for the patient exam, the practitioner's opinion of any patient conditions based on the practitioner hearing the heart sounds during auscultation and other parameters monitored during the patient exam (e.g., blood pressure), and a summary of the clinical findings output by the analysis system. The voice recording may be transcribed and the voice transcription may be formatted into patient notes, as explained above. The patient notes may then be sent to the external computing device where the patient notes may be displayed as part of the GUI. In some examples, the patient notes may include selectable links to allow the practitioner or another, subsequent practitioner to listen to the heart sound recording and/or view the ECG and/or PCG plots.

FIG. 7 shows an example processing pipeline 700 that may be employed by the dictation stethoscope 100 during the stethoscope mode. The processing pipeline 700 may be employed during the execution of method 400 and/or method 500. The output from the first microphone 122 and the second microphone 138 is received at the CPU 116 (which is in the form of an MCU in FIG. 7). The output from the first microphone 122 and the second microphone 138 may be processed at a converter 704, which may convert the digitized output of the microphones from a first format to a second format (e.g., from pulse-density modulation (PDM) to the I²S protocol). The output from the first microphone 122 and the second microphone 138 may then be further processed through a signal processing block 706 that includes an active noise cancellation (ANC) block. The ANC block may use the output of the second microphone 138 to cancel noise in the output of the first microphone 122 and results in the modified first signal explained above. The modified first signal (e.g., the output of the first microphone 122 after noise cancellation) is compressed at a compression block 708 to produce a physiological sound signal that is transmitted to one or more external devices, such as external computing device 140, via a suitable wireless transmission protocol (e.g., Bluetooth), at a first sampling rate (4 kHz) and a first resolution (e.g., 16 bit). The modified first signal may also be further processed (e.g., filtering, gain) and fed to an amplifier 710 to produce an analog audio signal that may be projected via speakers of the stethoscope (e.g., speaker(s) 104).

Figure 8:
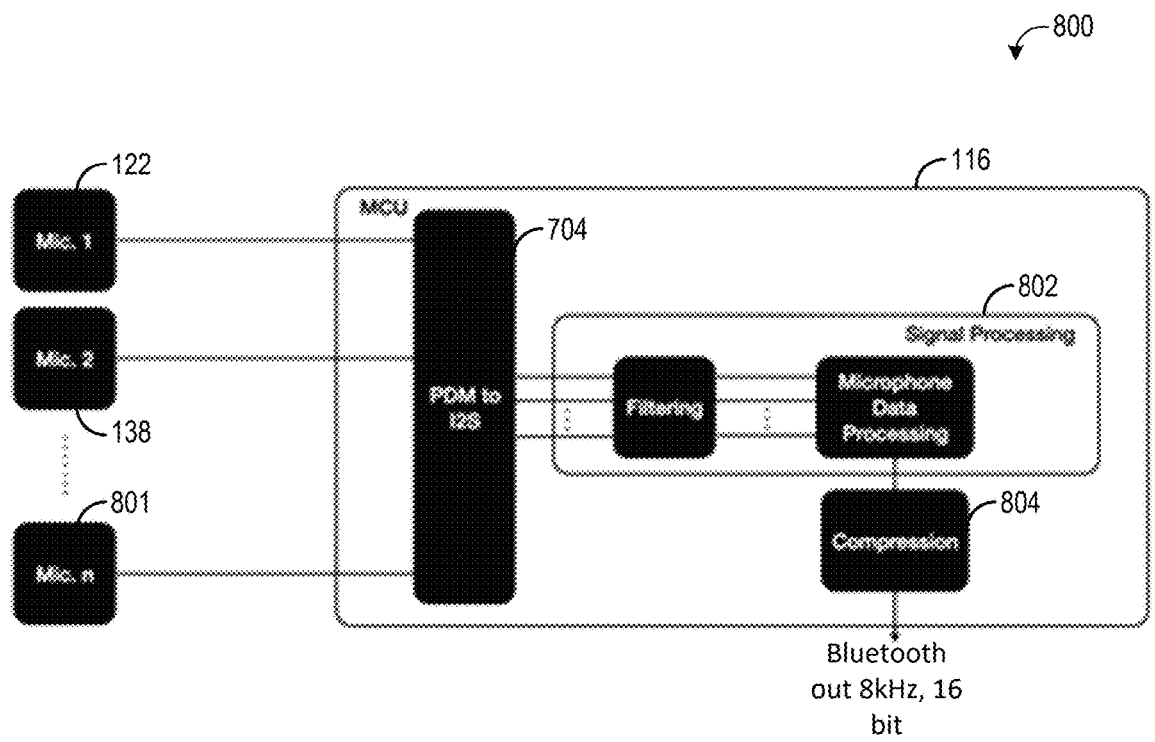

FIG. 8 shows an example processing pipeline 800 that may be employed by the dictation stethoscope 100 during the dictation mode. The processing pipeline 800 may be employed during the execution of method 400 and/or method 500. The output from the second microphone 138, as well as one or more additional microphones (e.g., first additional microphone 801) when an array of second microphones is included, is received at the CPU 116 (which is in the form of an MCU in FIG. 9). The output from the second microphone 138 and the additional microphones (e.g., first additional microphone 801) may be processed at the converter 704, as explained above with respect to FIG. 8. The output from the second microphone 138 and the additional microphones (e.g., a third microphone, such as first additional microphone 801) may then be further processed through a signal processing block 802 that includes a filtering block and a microphone data processing block. The filtering block may include a high-pass filter to remove low frequency content, which does not include useful information for voice. The microphone data processing block may perform the beamforming and/or beamsteering described above. The beamformed/beamsteered signal that is output from the microphone data processing block may be compressed at a compression block 804 to produce a voice signal that is transmitted to one or more external devices, such as external computing device 140, via a suitable wireless transmission protocol (e.g., Bluetooth), at a second sampling rate (8 kHz) and the first resolution (e.g., 16 bit). If the dictation stethoscope does not include an array of second microphones, the output from the filtering block may be compressed at the compression block 804. While the output from the first microphone 122 is shown in FIG. 8, it is to be appreciated that during dictation mode, the first microphone 122 may be deactivated or the output from the first microphone 122 may be discarded or ignored.

Figure 10A:
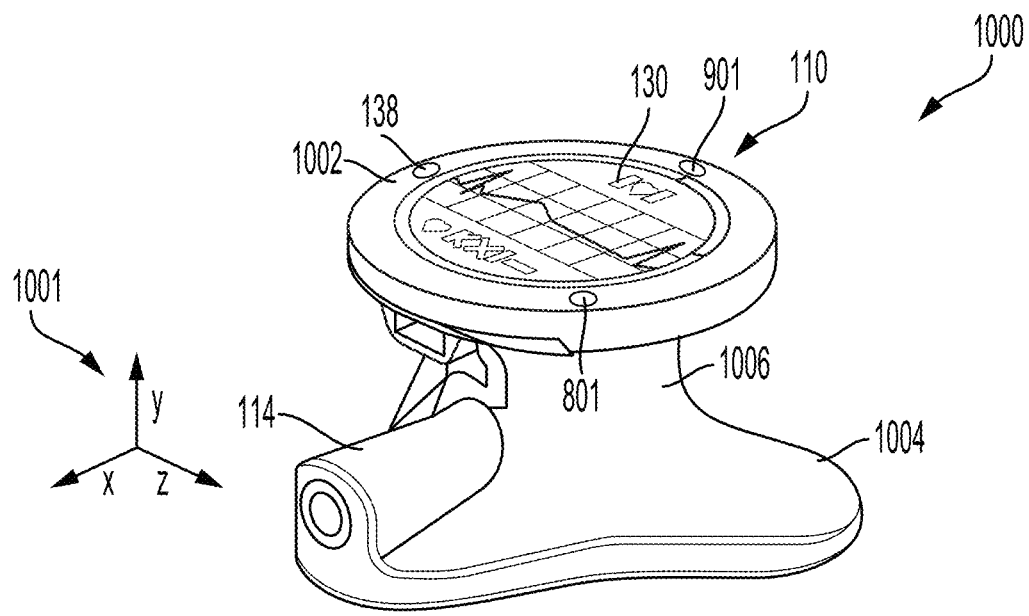
Figure 10B:
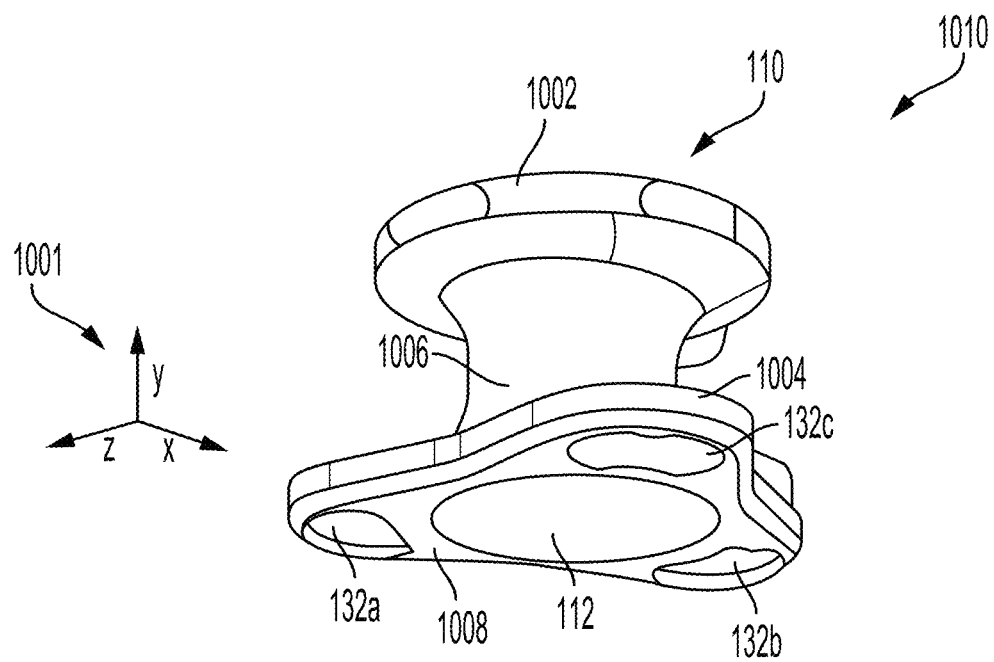

FIGS. 9, 10A, and 10B show example configurations of the chestpiece 110 including various external microphone array arrangements. FIG. 9 shows schematic views of the chestpiece 110 including a first array arrangement 900, a second array arrangement 910, and a third array arrangement 920. The first array arrangement 900 includes two external microphones (e.g., the second microphone 138 and the first additional microphone 801) positioned on a top of the chestpiece 110 in a linear arrangement at opposite sides of the chestpiece 110 (e.g., spaced 180° apart). The second array arrangement 910 includes three external microphones (e.g., the second microphone 138, the first additional microphone 801, and a second additional microphone 901) positioned on a top of the chestpiece 110 in a linear arrangement, with the second microphone 138 and the first additional microphone 801 at opposite sides of the chestpiece 110 (e.g., spaced 180° apart) and the second additional microphone 901 positioned intermediate and equidistant the second microphone 138 and the first additional microphone 801. The third array arrangement 920 includes four external microphones (e.g., the second microphone 138, the first additional microphone 801, the second additional microphone 901, and a third additional microphone 902) positioned on a top of the chestpiece 110 in a circular plus one arrangement, with the second microphone 138, the first additional microphone 801, and the second additional microphone 901 arranged around the outer circumference of the top of the chestpiece 110 (e.g., spaced 120° apart) and the third additional microphone 902 positioned in a center of the top of the chestpiece 110.

FIG. 10A shows a first view 1000 of the chestpiece 110 (e.g., a top perspective view) and FIG. 10B shows a second view 1010 of the chestpiece 110 (e.g., a bottom perspective view). Each of FIGS. 10A and 10B includes a Cartesian coordinate system 1001 to orient the views. In the coordinate system 1001, the y axis may be parallel to a direction of gravity. FIGS. 10A and 10B are described collectively. FIGS. 10A and 10B are shown to scale, though other relative dimensions may be used.

In the example shown in FIGS. 10A and 10B (which is non-limiting and other configurations are possible), chestpiece 110 is comprised of a top portion 1002, a bottom portion 1004, and a middle portion 1006 coupled intermediate the top portion 1002 and the bottom portion 1004. The top portion 1002 may be circular or have another suitable shape (e.g., oval, rectangular) and may include the display screen 130 on a top surface of the top portion 1002.

The bottom portion 1004 may include a bottom surface 1008 configured to be positioned against a patient during a patient exam to perform auscultation and/or obtain electrical signals of the heart (e.g., obtain ECG signals). The bottom surface 1008 of the bottom portion 1004 includes the diaphragm 112, which as shown in FIG. 10B is positioned in a center region of the bottom surface 1008. The bottom surface 1008 may further include electrodes 132 for obtaining ECG signals. In the example shown, three electrodes are included on the bottom surface 1008: a first electrode 132a, a second electrode 132b, and a third electrode 132c.

The chestpiece 110 as shown in FIGS. 10A and 10B includes a fourth array arrangement, with three external microphones arranged on the top surface of the top portion 1002 in a circular arrangement. For example, the second microphone 138, the first additional microphone 801, and the second additional microphone 901 may be arranged around an outer circumference of the top surface of the top portion 1002 (e.g., spaced 120° apart). In this way, the microphones for active noise cancellation and capturing voice recordings may be positioned on the chestpiece 110 at an opposite side of the chestpiece 110 as the diaphragm 112 (e.g., the external microphones may be on the top of the chestpiece while the diaphragm is on the bottom of the chestpiece), which may reduce contamination of the second signal (and signals captured from the additional microphones) from physiological sounds generated by the diaphragm 112. The microphones may be separated from each other by a distance to facilitate beamforming and beamsteering, as discussed above. Further, the top surface of the top portion 1002 may not be touched or gripped by a user frequently, as the user may grip the chestpiece 110 via the middle portion 1006 during auscultation. Thus, by positioning the external microphones on the top surface, noise contamination from a user touching the chestpiece 110 may be reduced while positioning the external microphones to capture ambient sounds. It is to be appreciated that each microphone shown in FIG. 10A may be positioned in a port and thus may be recessed relative to the top surface, but may still be positioned proximal the top surface. Further, the first microphone 122 may be positioned internally (e.g., near the diaphragm) and thus is not visible in FIGS. 10A and 10B.

FIGS. 1A-10B are described above with respect to a dictation stethoscope that includes one or more external microphones and one or more sensors for capturing patient monitoring data (e.g., a microphone for capturing physiological sounds and optionally one or more ECG electrodes). However, other medical devices could be configured as dictation devices using the same approaches described herein, such as blood pressure cuffs, pulse oximeters, thermometers, and the like. For example, a blood pressure cuff could include an external microphone and a sensor for measuring blood pressure. The external microphone may be activated when the blood pressure cuff is placed into a dictation mode. The blood pressure data collected with the sensor of the blood pressure cuff, along with the voice recording captured with the external microphone, could be transmitted to an external computing device and/or an analysis system, as explained above, for formatting into patient notes that include the blood pressure data (and where applicable, clinical findings based on the blood pressure data) and a voice transcription obtained from the voice recording.

A technical effect of using a medical device such as a digital stethoscope as a dictation device is that a conversation between a patient and a medical practitioner may be recorded and transcribed into a text-based transcription without demanding additional hardware, software, or personnel and while maintaining patient privacy and device security protocols. Further, the dictation stethoscope may be specially configured to facilitate collection of both physiological sounds and voice recordings, including specific arrangement of an internal microphone (e.g., near a diaphragm of the stethoscope) and one or more external microphones (e.g., separated from the diaphragm, such as on an opposite side of the chestpiece from the diaphragm) and specific signal processing features (e.g., active noise cancellation using a signal from the external microphone, beamforming or beamsteering using an array of external microphones, filtering) to strengthen the signals of the physiological sound recording and of the voice recording. Further, the processing of the captured signals may be differential depending on whether the stethoscope is operating in stethoscope mode or dictation mode, including different sampling rates for sampling the microphones for the physiological sound signal versus the voice signal, different compression techniques for compressing the physiological sound signal versus the voice signal, and different filtering of the physiological sound signal versus the voice signal.

The disclosure also provides support for a dictation stethoscope, comprising: a first microphone positioned to capture physiological sounds of a patient, a second microphone positioned to capture ambient sounds in an environment surrounding the dictation stethoscope, one or more processors, and memory storing instructions executable by the one or more processors to: during a stethoscope mode, obtain a first signal from the first microphone and a second signal from the second microphone, process the first signal to capture a physiological sound signal, the processing including performing noise cancellation on the first signal based on the second signal, and transmit the physiological sound signal to an external computing device and/or a speaker of the dictation stethoscope, and during a dictation mode, obtain the second signal from the second microphone, process the second signal to capture a voice signal, and transmit the voice signal to the external computing device. In a first example of the stethoscope, processing the first signal includes downsampling the first signal such that the physiological sound signal has a first sampling rate that is lower than a second sampling rate of the voice signal. In a second example of the stethoscope, optionally including the first example, processing the first signal comprises performing the noise cancellation to form a modified first signal and compressing the modified first signal with a first compression process to capture the physiological sound signal, and wherein processing the second signal comprises compressing the second signal with a second compression process to capture the voice signal, wherein the first compression process is different than the second compression process. In a third example of the stethoscope, optionally including one or both of the first and second examples, the first compression process is a lossless compression process and the second compression process is a lossy compression process. In a fourth example of the stethoscope, optionally including one or more or each of the first through third examples, during the dictation mode, the first microphone is deactivated or the first signal from the first microphone is discarded. In a fifth example of the stethoscope, optionally including one or more or each of the first through fourth examples, the stethoscope further comprises: a third microphone positioned to capture ambient sounds in the environment, and wherein processing the second signal comprises performing beamforming and/or beamsteering with the second signal and a third signal obtained from the third microphone. In a sixth example of the stethoscope, optionally including one or more or each of the first through fifth examples, the stethoscope further comprises: an electrocardiogram (ECG) sensor positioned to capture electrical activity of a heart of the patient, and wherein the instructions are further executable by the one or more processors to, during the stethoscope mode, obtain an ECG signal from the ECG sensor and transmit the ECG signal to the external computing device. In a seventh example of the stethoscope, optionally including one or more or each of the first through sixth examples, the stethoscope further comprises: using patient information captured in the voice signal to inform an analysis of ECG signal and/or physiological sound signal. In an eighth example of the stethoscope, optionally including one or more or each of the first through seventh examples, the analysis of ECG signal and/or physiological sound signal is used to generate a note detailing findings of an exam of the patient, and the note is incorporated in patient summary notes generated from the voice signal.

The disclosure also provides support for a system, comprising: a medical device including an external microphone for capturing a voice recording and one or more sensors for capturing patient monitoring data of a patient, and an analysis system including instructions stored in memory and one or more processors configured to execute the instructions to: receive the patient monitoring data and the voice recording from the medical device, automatically generate patient notes that include a voice transcription of the voice recording and the patient monitoring data, and save the patient notes in long-term storage and/or push the patient notes to an electronic medical record (EMR) system. In a first example of the system, the one or more processors are further configured to execute the instructions to identify the patient from the voice transcription and include information that identifies the patient in the patient notes. In a second example of the system, optionally including the first example, the one or more processors are further configured to execute the instructions to identify one or more clinical findings from the patient monitoring data and include the one or more clinical findings in the patient notes. In a third example of the system, optionally including one or both of the first and second examples, the one or more processors are further configured to execute the instructions to send the patient notes and/or the patient monitoring data to an external computing device for display on the external computing device. In a fourth example of the system, optionally including one or more or each of the first through third examples, the medical device is a stethoscope, wherein the one or more sensors include an internal microphone, and wherein the patient monitoring data comprises a physiological sound recording captured with the internal microphone. In a fifth example of the system, optionally including one or more or each of the first through fourth examples, the one or more sensors further include one or more electrocardiogram (ECG) electrodes and the patient monitoring data further includes one or more ECG plots.

The disclosure also provides support for a method, comprising: operating a dictation stethoscope in a stethoscope mode, including obtaining a first signal from first microphone of the dictation stethoscope and a second signal from a second microphone of the dictation stethoscope, processing the first signal to form a physiological sound signal, the processing including performing noise cancellation on the first signal based on the second signal, and transmitting the physiological sound signal to an external computing device and/or a speaker of the dictation stethoscope, and receiving a user input requesting to operate in a dictation mode, and in response, operating the dictation stethoscope in the dictation mode, including obtaining the second signal from the second microphone, processing the second signal to form a voice signal, and transmitting the voice signal to the external computing device. In a first example of the method, receiving the user input comprises receiving a user input to a button of the dictation stethoscope. In a second example of the method, optionally including the first example, transmitting the voice signal to the external computing device comprises transmitting the voice signal in real-time to the external computing device. In a third example of the method, optionally including one or both of the first and second examples, transmitting the voice signal to the external computing device comprises storing the voice signal in memory until a second user input is received indicating to cease operation in the dictation mode, and then transmitting the voice signal to the external computing device in response to receiving the second user input. In a fourth example of the method, optionally including one or more or each of the first through third examples, processing the first signal comprises performing the noise cancellation to form a modified first signal and compressing the modified first signal with a first compression process to form the physiological sound signal, and wherein processing the second signal comprises compressing the second signal with a second compression process to form the voice signal, wherein the first compression process is different than the second compression process.

Certain adaptations and modifications of the described embodiments can be made. Therefore, the above discussed embodiments are considered to be illustrative and not restrictive. The present disclosure is not to be limited in scope by the specific embodiments described herein. Further example embodiments may also include all of the steps, features, and components referred to or indicated in this description, individually or collectively and any and all combinations or any two or more of the steps or features.

The following claims particularly point out certain combinations and sub-combinations regarded as novel and nonobvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A dictation stethoscope comprising a body having a top surface and a bottom surface opposite the top surface, comprising:
   a first microphone positioned to capture physiological sounds of a patient, the first microphone positioned inside the body such that the first microphone translates vibrations due to movement of a diaphragm of the stethoscope into a first signal, the diaphragm located at the bottom surface;

a second microphone positioned to capture ambient sounds in an environment surrounding the dictation stethoscope, the second microphone positioned at the top surface;

one or more processors; and memory storing instructions executable by the one or more processors to:

during a stethoscope mode, obtain the first signal from the first microphone and a second signal from the second microphone, process the first signal to capture a physiological sound signal, the processing including performing noise cancellation on the first signal based on the second signal, and transmit the physiological sound signal to an external computing device and/or a speaker of the dictation stethoscope; and during a dictation mode, obtain the second signal from the second microphone, process the second signal to capture a voice signal, and transmit the voice signal to the external computing device, wherein during the dictation mode, the first microphone is deactivated.

2. The dictation stethoscope of claim 1, wherein processing the first signal includes downsampling the first signal such that the physiological sound signal has a first sampling rate that is lower than a second sampling rate of the voice signal, and wherein the second signal is not downsampled.

3. The dictation stethoscope of claim 1, wherein processing the first signal comprises performing the noise cancellation to form a modified first signal and compressing the modified first signal with a first compression process to capture the physiological sound signal, and wherein processing the second signal comprises compressing the second signal with a second compression process to capture the voice signal, wherein the first compression process is different than the second compression process.

4. The dictation stethoscope of claim 3, wherein the first compression process is a lossless compression process and the second compression process is a lossy compression process.

5. The dictation stethoscope of claim 1, further comprising a third microphone positioned to capture ambient sounds in the environment, wherein processing the second signal comprises performing beamforming and/or beamsteering with the second signal and a third signal obtained from the third microphone, and wherein the third microphone is positioned at the top surface.

6. The dictation stethoscope of claim 1, further comprising an electrocardiogram (ECG) sensor positioned to capture electrical activity of a heart of the patient, wherein the instructions are further executable by the one or more processors to, during the stethoscope mode, obtain an ECG signal from the ECG sensor and transmit the ECG signal to the external computing device, wherein the ECG sensor includes first electrode, a second electrode, and a third electrode each positioned at the bottom surface, and wherein the diaphragm is positioned in a center region of the bottom surface and the first electrode, the second electrode, and the third electrode are positioned around an outer circumference of the diaphragm.

7. The dictation stethoscope of claim 6, further comprising using patient information captured in the voice signal to inform an analysis of ECG signal and/or physiological sound signal.

8. The dictation stethoscope of claim 7, where the analysis of ECG signal and/or physiological sound signal is used to generate a note detailing findings of an exam of the patient; and the note is incorporated in patient summary notes generated from the voice signal.

9. A system, comprising:

a medical device including a body having a top surface and a bottom surface opposite the top surface, an external microphone positioned at the top surface for capturing a second signal and an internal microphone in the body for capturing a first signal data of a patient, wherein the internal microphone translates vibrations due to movement of a diaphragm of the medical device into the first signal, the diaphragm located at the bottom surface, wherein the medical device is configured to operate in a stethoscope mode wherein the first signal is processed to capture a physiological sound recording of a patient and in a dictation mode wherein the second signal is processed to capture a voice recording, wherein during the dictation mode, the internal microphone is deactivated or the first signal from the internal microphone is discarded, and wherein processing the first signal includes downsampling the first signal such that the physiological sound recording has a first sampling rate that is lower than a second sampling rate of the voice recording; and an analysis system including instructions stored in memory and one or more processors configured to execute the instructions to:

receive the physiological sound recording and the voice recording from the medical device;

automatically generate patient notes that include a voice transcription of the voice recording and the physiological sound recording; and save the patient notes in long-term storage and/or push the patient notes to an electronic medical record (EMR) system.

10. The system of claim 9, wherein the one or more processors are further configured to execute the instructions to identify the patient from the voice transcription and include information that identifies the patient in the patient notes.

11. The system of claim 9, wherein the one or more processors are further configured to execute the instructions to identify one or more clinical findings from the physiological sound recording and include the one or more clinical findings in the patient notes.

12. The system of claim 9, wherein the one or more processors are further configured to execute the instructions to send the patient notes and/or the physiological sound recording to an external computing device for display on the external computing device.

13. The system of claim 9, wherein the medical device includes one or more electrocardiogram (ECG) electrodes and the patient notes further include one or more ECG plots generated from data captured by the one or more ECG electrodes, wherein the one or more ECG sensors are positioned on the bottom surface, wherein processing the first signal comprises performing noise cancellation using the second signal captured during the stethoscope mode to form a modified first signal and compressing the modified first signal with a first compression process to capture the physiological sound recording, and wherein processing the second signal comprises compressing the second signal with a second compression process to capture the voice recording, and wherein the first compression process is different than the second compression process.

14. A method, comprising:
  operating a dictation stethoscope in a stethoscope mode, including obtaining a first signal from first microphone of the dictation stethoscope and a second signal from a second microphone of the dictation stethoscope, processing the first signal to form a physiological sound signal, the processing including performing noise cancellation on the first signal based on the second signal, and transmitting the physiological sound signal to an external computing device and/or a speaker of the dictation stethoscope; and
  receiving a user input requesting to operate in a dictation mode, and in response, operating the dictation stethoscope in the dictation mode, including obtaining the second signal from the second microphone, processing the second signal to form a voice signal, and transmitting the voice signal to the external computing device, wherein during the dictation mode, the first microphone is deactivated, and wherein processing the first signal includes downsampling the first signal such that the physiological sound signal has a first sampling rate that is lower than a second sampling rate of the voice signal.

15. The method of claim 14, wherein receiving the user input comprises receiving the user input to a button of the dictation stethoscope.

16. The method of claim 14, wherein transmitting the voice signal to the external computing device comprises transmitting the voice signal in real-time to the external computing device.

17. The method of claim 14, wherein transmitting the voice signal to the external computing device comprises storing the voice signal in memory of the dictation stethoscope until a second user input is received indicating to cease operation in the dictation mode, and then transmitting the voice signal to the external computing device in response to receiving the second user input.

18. The method of claim 14, wherein processing the first signal comprises performing the noise cancellation to form a modified first signal and compressing the modified first signal with a first compression process to form the physiological sound signal, and wherein processing the second signal comprises compressing the second signal with a second compression process to form the voice signal, wherein the first compression process is different than the second compression process.

19. The method of claim 14, further comprising:
  reactivating the first microphone responsive to a request to operate in the stethoscope mode.

20. The method of claim 14, further comprising:
  deactivating the first microphone and the second microphone responsive to powering off of the dictation stethoscope; and
  responsive to entering a standby mode, not capturing the first signal or the second signal and powering down one or more components of the dictation stethoscope while the dictation stethoscope continues to be powered on.

\* \* \* \* \*